United States Patent [19]

Gompper et al.

[11] Patent Number: 5,507,974
[45] Date of Patent: Apr. 16, 1996

[54] AROMATIC, SUBSTITUTED PYRIMIDINE COMPOUNDS, METHODS FOR THE PREPARATION THEREOF, AND USE THEREOF

[75] Inventors: Rudolf Gompper; Harald Engel, both of Munich; Donald Lupo, Eppstein, all of Germany

[73] Assignee: Hoechst Aktiengesellschaft, Germany

[21] Appl. No.: 164,145

[22] Filed: Dec. 9, 1993

[30] Foreign Application Priority Data

Dec. 11, 1992 [DE] Germany .................. 42 41 806.2

[51] Int. Cl.$^6$ ............ C09K 19/52; C09K 19/34; C07D 239/02
[52] U.S. Cl. .............. 252/299.01; 252/299.61; 359/103; 544/297; 544/298; 544/300; 544/301; 544/302; 544/328; 544/331; 544/332; 544/333; 544/335
[58] Field of Search ............ 252/299.01, 299.61; 359/103; 544/297, 298, 300, 301, 302, 328, 331, 332, 335

[56] References Cited

FOREIGN PATENT DOCUMENTS

| | | |
|---|---|---|
| 175591 | 3/1986 | European Pat. Off. . |
| 541081 | 5/1993 | European Pat. Off. . |
| 04300869 | 10/1992 | Japan . |
| 858316 | 11/1985 | U.S.S.R. . |

OTHER PUBLICATIONS

CA110:212742, 1988.
CA:73:98890, 1970.

*Primary Examiner*—Shean C. Yu
*Attorney, Agent, or Firm*—Curtis, Morris & Safford

[57] ABSTRACT

Aromatic, substituted pyrimidine compounds, methods for the preparation thereof, and use thereof Compounds having a pyrimidine ring, of the formula (I)

$$AX-\text{Ar}-B-\text{Ar}-D \quad (I)$$

are suitable for nonlinear-optical applications, e.g. for fabricating components for frequency-doubling of light. In the formula, AX is $$NO_2-C\!\!\!\!\!/\,, \quad R^1OCO-C\!\!\!\!\!/\,, \quad R^1CO_2-C\!\!\!\!\!/\,,$$

$$R^2CO-C\!\!\!\!\!/\,, \quad N\!\!\!\!\!/\,, \quad R^3-\overset{(+)}{N}\!\!\!\!\!/\, An^-,$$

$$\underset{CN}{\overset{CN}{\diagdown}}\!\!\!\!\!\overset{(-)}{C}\!\!-\!\!\overset{(+)}{N}\!\!\!\!\!/\,, \quad R^1SO_2-C\!\!\!\!\!/\,,$$

$An^-$ is an anion, B is the pyrimidine(1,4) radical, D is —$NH_2$, —$NH$—$NH_2$, —$OR^6$, —$O(CH_2)_pOH$, —OH, —$NR^5R^6$, —$NHR^6$, —N=CH—$R^4$, —HN—N=CH—$R^4$, —$NO_2$,
the radicals $R^1$, $R^2$, $R^3$ and $R^5$ are an alkyl radical having from 1 to 22 carbon atoms or a radical $CF_3(CF_2)_m(CH_2)_n$, $R^4$ is a phenyl radical which may be substituted, $R^6$ is an alkyl radical having from 1 to 22 carbon atoms or the radical $CF_3(CF_2)_m(CH_2)_n$, where m is an integer of at least 5, n is an integer of at least zero, and (n+m) is at most 22, or the group $(CH_2)_pOH$, where p is an integer from 2 to 5.

26 Claims, 4 Drawing Sheets

AROMATIC, SUBSTITUTED PYRIMIDINE COMPOUNDS, METHODS FOR THE PREPARATION THEREOF, AND USE THEREOF

The invention relates to compounds which are derived from a pyrimidine which is substituted in the 2-position and the 5-position by phenyl rings and/or pyridine rings, and to processes for the preparation of these compounds. The invention also relates to layer elements which contain these compounds in the form of monomolecular layers on a support, and to the use of the compounds for purposes of nonlinear optics.

Because of the pyrimidine ring, the molecules of the said compounds are non-centrosymmetrical. They will therefore usually have a dipole moment. They also have an extended $\pi$-electron system. Most of the compounds in addition also contain typical donor and acceptor radicals. All of this makes them suitable for purposes of nonlinear optics.

Nonlinear optics (NLO) make it possible, inter alia, by means of suitable instruments to obtain from two light beams of different frequency a new frequency which corresponds to the difference or the sum and to obtain from a light beam of one optical frequency optical signals having a multiple of this frequency (in particular twice this frequency). Nonlinear optics also allow electrical information to be converted into optical information and may therefore lead in the long term to a fundamental change in the technology of data transmission and data storage.

NLO materials are suitable for the preparation of nonlinear optical components, for example electro-optical modulators, electro-optical switches, electro-optical directional couplers and frequency doublers. These components are used, for example, in optical communications technology (for modulating and controlling optical signals), as spatial light modulators in optical signal processing, for frequency-doubling of semiconductor lasers, for optical data storage, sensor technology and xerography.

A large number of inorganic crystals such as, for example, potassium dihydrogenphosphate and lithium niobate have been investigated as NLO materials. Modulators composed of lithium niobate and frequency doublers based on potassium dihydrogenphosphate are commercially available.

In addition, however, organic NLO materials are of great interest. There are several reasons for this. On the one hand, the NLO activity (=NLO susceptibility) of organic materials is frequently much higher than in the case of inorganic materials. The refractive index and the dielectric constant are in general lower. This allows larger internal electric fields, small polarizations and lower reflection losses, all of which lead to higher efficiency.

Organic materials can also be prepared by a "tailor-made" synthesis, for example with the object of obtaining materials having a high transparency at a defined working wavelength. Organic materials can be processed in many ways. The preparation of monomolecular films of organic materials is simpler than, for example, the preparation of inorganic crystals. These crystals must be grown at relatively high temperatures, then cut, polished and oriented. There is therefore a demand for organic materials which exhibit second-order and third-order NLO effects.

The (macroscopic) polarization P induced in a medium by an electric field can be expanded in a power series of the electric field strength E.

$$P = X^{(1)}E + X^{(2)}E^2 + X^{(3)}E^3 + \ldots$$

The $X^{(i)}$ are the so-called electric susceptibility functions. The susceptibilities $X^{(2)}$ and $X^{(3)}$ depend on the so-called molecular hyperpolarizabilities $\beta$ and $\gamma$.

$$X^{(2)}(-\omega 3, \omega 2, \omega 1)_{XYZ} = N f_{x,\omega 3} f_{Y,\omega 2} f_{Z,\omega 1} D_{XYZxyz} \beta_{xyz}$$

$$P_1 = \alpha E + \beta E^2 + \gamma E^3 + \ldots$$

$P_1$ is here the polarization of the molecule; $\alpha$, $\beta$ and $\gamma$ are polarizabilities. N is the number of molecules per unit volume, f is the local field factor and $D_{XYZxyz}$ is a tensor which describes the orientations of the molecules in the macroscopic system.

As a result of NLO interactions, new frequencies can be generated in an NLO medium, and the refractive index of the medium can be changed.

Important nonlinear optical effects depending on $X^{(2)}$ are the frequency-doubling of a laser beam, the parametric amplification of a weak light signal and the electro-optical conversion of electric signals. To generate second-order effects, the active molecules must be oriented non-centrosymmetrically, since $X^{(2)}$ becomes=0 for centrosymmetrical molecules or crystals.

Attempts can be made to grow crystals of the NLO compounds. If these crystallize non-centrosymmetrically, the crystal has (without further treatment) a nonvanishing macroscopic second-order susceptibility $X^{(2)}$. With crystals, a very high concentration of the chromophore and a very high order are achieved, and also there are no problems with relaxation of the order, since the non-centrosymmetrical order represents the state of lowest free energy. However, the processability of many crystals is poor and the production of integrated optical components with single crystals is in most cases impractical. Moreover, non-centrosymmetrical molecules can also lead to centrosymmetrical crystals.

The process of generating thin layers according to Langmuir-Blodgett (=LB process) probably allows the widest freedom in chemical planning, but it requires extensive experience. In this process, molecules are spread on a water surface, arranged in parallel by reducing the area per molecule and, with constant shear, applied to a substrate by immersing a support and withdrawing it. One monomolecular layer is transferred per dipping step, while maintaining its order. For building up LB layers, amphiphilic molecules are used, i.e. molecules which have a hydrophilic end (a "head") and a hydrophobic end (a "tail").

In order to provide LB layers having high second-order susceptibilities, organic compounds are prepared which have both high molecular second-order hyperpolarizabilities $\beta$ and amphiphilic properties.

If an amphiphilic material composed of a single molecule species is arranged in multilayers by the LB process, three different possibilities of the dipping behavior can occur: films of the X type (transfer only during immersion) or of the Z type (transfer only during withdrawal) can occur, which both have the advantage of the non-centrosymmetrical structure. In most cases, however, films of the Y type are obtained (transfer during immersion and withdrawal), in which the molecules show a head-head and tail-tail arrangement.

In most cases, Y-type films show a centrosymmetrical structure. In the few compounds which have an orientation in the support plane (i.e. which have a non-centrosymmetrical structure), the achievable susceptibility is relatively low. In order to obtain a multilayer arrangement of non-centrosymmetrical structure with compounds which lead to Y-type films, three strategies can be applied:

a) A film is formed in which active layers and inactive layers (amphiphilic molecules without chromophore or polymers without chromophore, for example trimethylsilylcellulose or polymethylmethacrylates) alternate.

This method has the disadvantage that the NLO-active molecules do not efficiently exploit the available volume, since the inactive layers lead to a "dilution" of the system. Such films therefore show a lower NLO activity.

b) The transfer process is controlled in such a way that Z-type films are obtained. This requires, however, special multi-chamber installations for the coating of the substrates. Immersion and removal take place in different chambers.

c) Films of two different NLO-active amphiphilics, whose dipole moments are in one case pointing to the hydrophobic long-chain alkyl radical (tail) and, in the other case, face away from the latter, are alternately transferred. In this case the dipole moments of two adjoining layers will not cancel out, in spite of the Y structure, but will add to one another. The effective dipole moment is therefore still of an order of magnitude which makes it of interest for NLO purposes. If, for example, monolayers of the molecules A* and B* or B* and C*

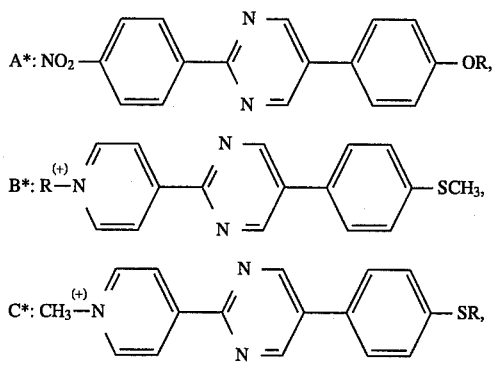

R in the formulae in each case being the n-octadecyl radical, are applied alternately (in a multichamber apparatus) a head-head and tail-tail arrangement will result. The dipole moments of adjacent molecules nevertheless have the same direction.

In doing so, two different chromophores can be employed in adjacent layers (molecules A and B), or the same chromophore (molecules B and C) can be used. In both cases, the hydrophobic group in the one layer is bound to the donor side and in the other to the acceptor side. In the second case, both the sterical requirements and the electrostatic interactions are similar for both layers. The packing of the layers should therefore be better and the NLO activity should become larger.

It is always desirable that the NLO-active compound has the largest possible optical nonlinearity $\beta$ (=second-order hyperpolarizability). A compound has a large $\beta$ value if it contains a conjugated $\pi$-electron system (for example the stilbene radical) and if there is at least one electron donor and at least one electron acceptor group. The value of $\beta$ is enhanced if the molecule absorbs light in the wave region of the incident electric field or of the field generated by NLO (so-called resonance amplification). However, absorptions are undesirable for many applications since they cause losses and adversely affect the optical stability. A compound is regarded as "optically stable" if it can endure the light intensity for a prolonged period without permanent damage to the material. An ideal compound would have a high hyperpolarizability $\beta$, but no residual absorption in the desired wavelength region. However, most compounds having a sufficiently high value for $\beta$ still show considerable residual absorption at the wavelengths desired for frequency-doubling, in particular in the region of 415 nm, which is obtained by frequency doubling of IR light of wavelength 830 nm (diode laser).

The object of the invention therefore is to provide organic compounds which have a chromophore and whose absorption maximum is below 400 nm, in particular below 350 nm, and which at the same time have good stability (toward the atmosphere, toward elevated temperatures and light) and a high NLO activity.

Novel aromatic compounds having a pyrimidine ring have now been found, which have the following formula (I)

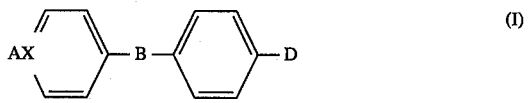

in which AX is

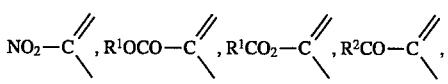

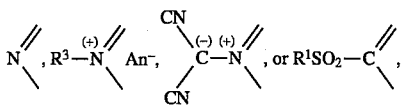

An⁻ is an anion

B is

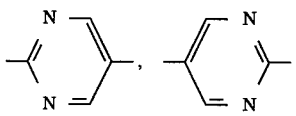

D is —NH$_2$, —NH—NH$_2$, —OR$^6$, —O(CH$_2$)$_p$OH, —OH, —NR$^5$R$^6$, —NHR$^6$, —N=CH—R$^4$, —HN—N=CH—R$^4$ or —NO$_2$, the radicals R$^1$, R$^2$, R$^3$, R$^5$ and R$^6$ are an alkyl radical having from 1 to 22 carbon atoms or a radical CF$_3$(CF$_2$)$_m$(CH$_2$)$_n$, where m is an integer of at least 5, n is an integer of at least zero, and (n+m) is at most 22, R$^4$ is a phenyl radical which may be substituted, the radicals R$^3$ and R$^6$ may alternatively be the group —(CH=)$_p$OH, and p is an integer from 2 to 5, especially from 2 to 3. The radical R$^4$ is, for example, m-alkylphenyl, p-alkoxyphenyl, p-dimethylaminophenyl, m-(ω-hydroxyalkyl)phenyl, where the alkyl chains may contain from 1 to 22 carbon atoms.

These compounds in general have no absorption or only a very small absorption in the visible range. The only exception are the pyridinium dicyanomethides which are orange to red. These compounds are therefore suitable not so much for frequency-doubling of light of a diode laser as for use in a light modulator. Most of the compounds have both an acceptor group and a donor group.

Those compounds, in which D is NO$_2$ and AX is

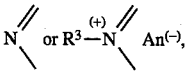

however contain two acceptor groups.

According to an advantageous embodiment of the invention, the novel compounds have the formula II

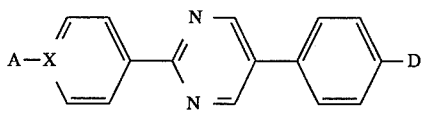  (II)

wherein AX is

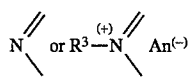

and
D is
OR$^6$, OH, NH$_2$, —NH—NH$_2$,
R$^4$—CH=N— or
R$^4$—CH=N—NH—.

The central pyrimidine ring may however be orientated differently with respect to the ring having the group AX.

According to another advantageous embodiment of the invention, the novel compounds have the formula III

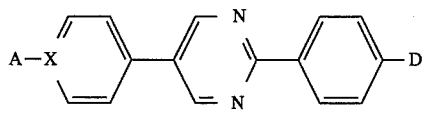  (III)

wherein AX is

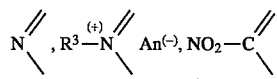

and D is OR$^6$ or —N=CH—R$^4$.

Compounds of the formula II have a total dipole moment higher than that of the isomeric compounds of the formula III, as the individual dipole moments of substituents and pyrimidine central unit are parallel.

In addition, compounds of the formula IV

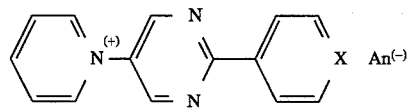  (IV)

were found, wherein X is

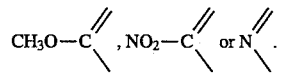

For reasons of electroneutrality, the compounds of the formula IV further contain an anion An$^{(-)}$, e.g. iodide, methyl sulfate, chloride or tetrafluoroborate. This also applies to the compounds of the formulae I to III, if the group AX is

In order to prepare compounds of the formula V

  (V)

wherein

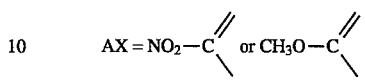

and
D=OCH$_3$, NO$_2$, or OH, a vinamidinium salt of the formula VI

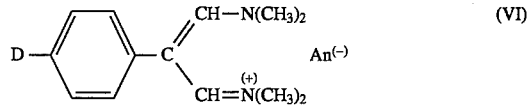  (VI)

wherein D is OCH$_3$, NO$_2$ or OH, is reacted with a benzamidine hydrochloride of the formula VII

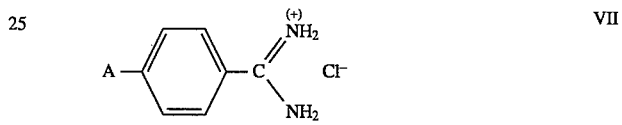  VII wherein A is NO$_2$ or OCH$_3$, in anhydrous pyridine.

In order to prepare compounds of the formula VIII

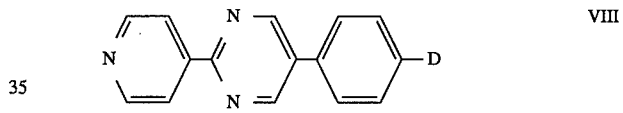  VIII wherein D =OCH$_3$, NO$_2$, or OH, a vinamidinium salt of the formula IX

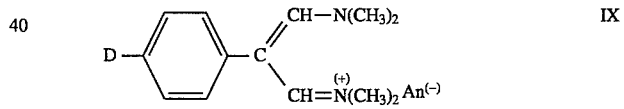  IX wherein D is OCH$_3$, NO$_2$ or OH, is reacted with 4-pyridinecarbamidine hydrochloride (formula X)

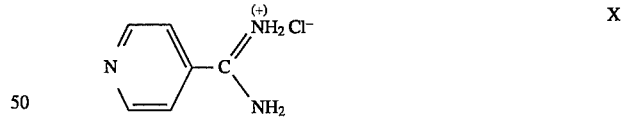  X in methanolic sodium methylate solution.

In order to prepare compounds of the formula (XI)

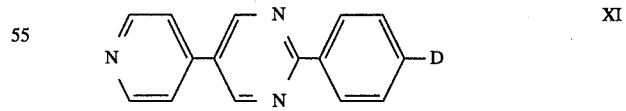  XI wherein D =OCH$_3$ or NO$_2$, a vinamidinium salt of the formula XII

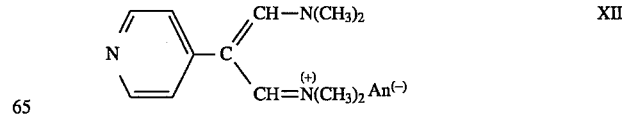  XII wherein D is NO$_2$ or OCH$_3$, is reacted with a benzamidine hydrochloride of the formula XIII

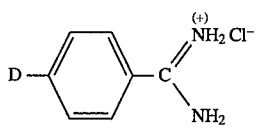 XIII in methanolic sodium methylate solution.

Phenolic OH groups can be reacted with alkyl bromides, carboxylic acid chlorides and epoxides. In doing so, alkyl phenol ethers can be obtained whose alkyl chain is longer than $C_1$, or compounds of the formula I in which AX is

or compounds of the formula I in which D is $O(CH_2)_pOH$ with p=2 or 3.

Nitro groups can be converted into amino groups by reduction with $SnCl_2$. These react with aromatic aldehydes to form Schiff bases and with alkyl iodides to give compounds of the formula I in which the radical D is a monoalkyl- or dialkylamino group.

From the amino compound, the corresponding hydrazino compounds can be obtained by diazotization and reduction with $SnCl_2$, and from these, with aromatic aldehydes, the corresponding hydrazones.

The pyridine compounds can be quaternized with alkyl iodide or dimethyl sulfate. The reaction with tetracyanoethylene epoxide gives the N-dicyanomethide compounds.

The pyrimidine derivatives obtained usually show strong solvatochromism. This suggests that the molecular hyperpolarizability β attains large values and the compounds are suitable for NLO.

Compounds of the formula I in which AX is

and

R³ is an alkyl radical having from 7 to 22 carbon atoms or the radical $CF_3(CF_2)_m(CH_2)_n$, wherein m is at least 5, n is at least zero and (n+m) is at most 22, have a long-chain hydrophobic end and a hydrophilic group.

This is also true of compounds of the formula I in which D is

OR², —N=CHR⁴, NR⁵R⁶, or —NH—N=CHR⁴ and the radicals

R² and R⁵ are an alkyl radical having from 4 to 22 carbon atoms, especially from 7 to 22 carbon atoms or the radical $CF_3$—$(CF_2)_m$—$(CH_2)_n$, m is at least 3, n is at least zero and (n+m) is at most 22, R⁴ is an alkylphenyl or alkoxyphenyl radical whose alkyl group contains from 4 to 22 carbon atoms and R⁶ is hydrogen or an alkyl radical having from 1 to 22 carbon atoms.

Such compounds can be arranged, according to the method by I. Langmuir and K. B. Blodgett, in the form of monomolecular multilayers on supports.

These compounds preferably have at one end an alkyl chain of from 18 to 22 carbon atoms and at the other end do not have an alkyl chain which contains more than one carbon atom, especially more than three carbon atoms.

In the non-linear optic device AX (formula (I)) can also be halogen

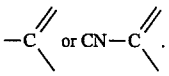

The invention therefore also relates to a layer element which contains at least one monomolecular layer composed of a compound of the formula I.

To prepare layer elements according to the invention with Langmuir-Blodgett films, the amphiphilic compounds are applied (spread) in a highly volatile solvent onto a clean water surface. The mean area per molecule can be calculated from the dimension of the surface, the spreading volume and the concentration of the solution. Phase transitions during the compression of the molecules can be monitored by the shear area isotherm.

By means of a barrier or by other techniques, for example utilization of hydrodynamic forces, the molecules are pushed together, the chains being oriented essentially perpendicular to the boundary layer as the density increases. During the compression, a highly ordered, monomolecular film, whose constant layer thickness is determined by the chain length of the molecules, is formed by self-organization of the molecules in the boundary layer. The typical thickness of such a film is between 2 and 3 nm.

Suitable supports are solids having clean surfaces, such as, for example, glass, ceramic plates or metal plates, plastic layers of, for example, PMMA, polystyrene, polycarbonate, polyethylene, polypropylene or polytetrafluoroethylene, or metal layers on the said substrates.

For an experimental determination of the value of the second-order susceptibility ($X^{(2)}$) in Langmuir-Blodgett films, the phenomenon of optical frequency-doubling can be used, in which a laser beam of frequency ω is converted in an active substance into a beam of frequency 2ω. In this case, the intensity of the generated harmonic at 2ω increases with the square of the incident intensity of the fundamental beam at ω. Most frequently, the method of the so-called "Maker Fringes" is used, which is briefly described here.

As the source of the electromagnetic wave at the angular frequency ω, typically an Nd:YAG laser is used which generates a brief (typically 30 ps–30 ns) light pulse at the wavelength 1064 nm (ω=9398 cm⁻¹). The light pulse is divided by a beam splitter into two beams in a sample channel and a reference channel. In the sample channel, the layer system to be measured is mounted on a turntable. A small part of the incident beam at 1064 nm is converted by the NLO-active system into a beam at 532 nm, i.e. at the doubled frequency. The intensity of the harmonic mode is measured by a photomultiplier, detected by data acquisition electronics and a control computer as a function of the angle of incidence and averaged over a plurality of shots per angle. Polarization elements and filters ensure that only the harmonic mode generated in the sample is measured under controlled polarization conditions.

An NLO-active substance, for example pulverulent 2-methyl-4-nitroaniline, is likewise mounted in the reference channel; it serves for compensating the scatter of the measured intensity, caused by fluctuations in the energy and the beam profiles in time and space. In the sample channel, a calibrated sample, for example a quartz crystal whose susceptibility is about 1 pm/V, is then measured. From the angle dependency of the harmonic intensity and the value of the latter as compared with the intensity of the calibrated sample, the NLO susceptibility and the information for orienting the chromophores can be obtained.

The NLO activity of a crystal, in particular a crystal composed of a compound according to the invention, can be investigated by the so-called Kurtz powder method. The compound to be investigated is comminuted in a mortar and retained in a layer about 0.2 mm thick between two microscope glass slides. A similar procedure is used with a reference sample (for example 2-methyl-4-nitroaniline). The samples are irradiated by a pulsed Nd:YAG laser, and the intensity of the forward-scattered light at 532 nm is measured by a photomultiplier for the sample and for the reference.

In donor-acceptor systems, the molecular hyperpolarizability $\beta$ can be estimated by determining the integrated intensity of the absorption band and the shift of the absorption maximum in different solvents. This method is based on the assumption that the optical nonlinearity is dominated by the charge shift between the ground state and the first electronically excited state. In this case, $\beta$ is proportional to the transition moment for the absorption of lowest energy, which can be determined by measuring the integrated band intensity. The hyperpolarizability is also proportional to the difference between the dipole moments of the two states. This difference can be estimated by the transfer of the absorption wavelength between two solvents having different dielectric constants.

The compounds according to the invention make it possible, especially if they are present as a Langmuir-Blodgett film in a layer element or in the form of a non-centrosymmetrical crystal, to prepare an optical system having good nonlinear optical properties. Such systems are suitable, for example, for electro-optical switches, diode laser frequency doublers or optical parametric amplifiers (for example as so-called boosters of weak light signals in optical signal transmission networks).

The figures which follow explain the principle of the construction of a corresponding component.

BRIEF DESCRIPTION OF FIGURES

FIG. 1 represents a component (100) for doubling the frequency of a lightwave. Between a substrate (layer support) 104 and a cover layer 105, the NLO-active layer 103 is embedded. The refractive index of (103) and (105) should be lower than that of 104, so that total reflection is possible.

Figure 1:
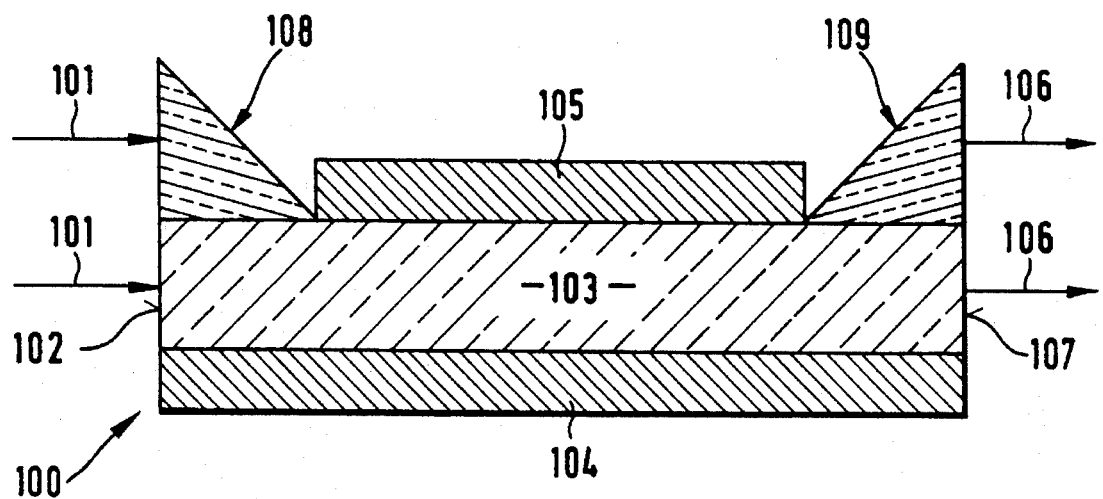
FIG. 1 shows an apparatus for doubling the frequency of a lightwave.

The light 101 (for example 830 nm) is launched through the end face 102 of the layer 103 or through a prism 108 or a grating (not shown). The cover layer (105) only serves to protect the active layer and can also be omitted. The active layer 103 can alternatively be laterally structured, so that the light is guided in two dimensions (perpendicular to and parallel to the layer plane).

The active layer contains a pyrimidine compound according to the invention, which preferably has a high (more than $10^{-8}$ esu) optical second-order susceptibility. If the thickness and width of the layer 103 and the refractive index of the substrate (104) are in the correct ratio to the wavelength of the incident light, the phase velocity of the dominant mode launched can be matched to that of the second harmonic mode. In that case, a particularly great quantity of light of double the frequency (for example 415 nm) is generated in (103). The light beam (106) leaves the NLO-active layer at the other end face (107) or via a prism (109) or a grating (not shown). The light of the incident wavelength can be removed from (106) by means of filters.

In an alternative version (not shown), the waveguide is constructed in such a way that the dominant mode launched is carried in the waveguide, but the harmonic mode is extracted according to the so-called Cerenkov principle into the substrate and leaves the latter at the end face thereof.

Figure 2:
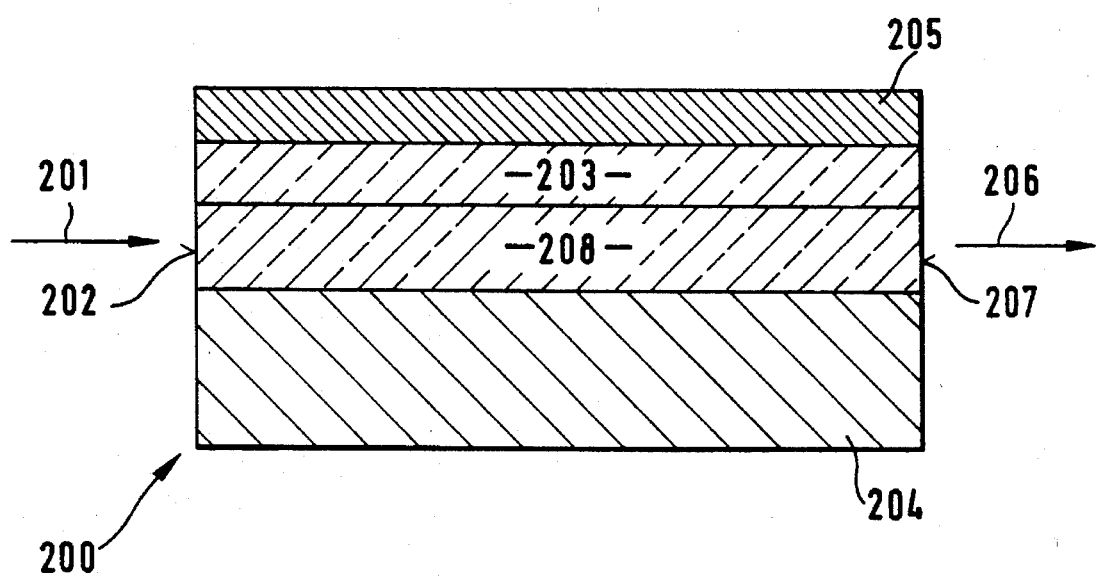
FIG. 2 shows an alterative embodiment of the apparatus of FIG. 1.

FIG. 2 shows an alternative embodiment for this component, with substrate 204 and cover layer 205. The incident light beam 201 enters analogously through the end face 202. The light beam with additional frequency (206) leaves the component through the end face 207. The waveguide is in this case composed of an NLO-inactive layer (203) of high refractive index and an NLO-active layer 208, which contains the compound according to the invention, in particular in the form of an LB multilayer.

Figure 3A:
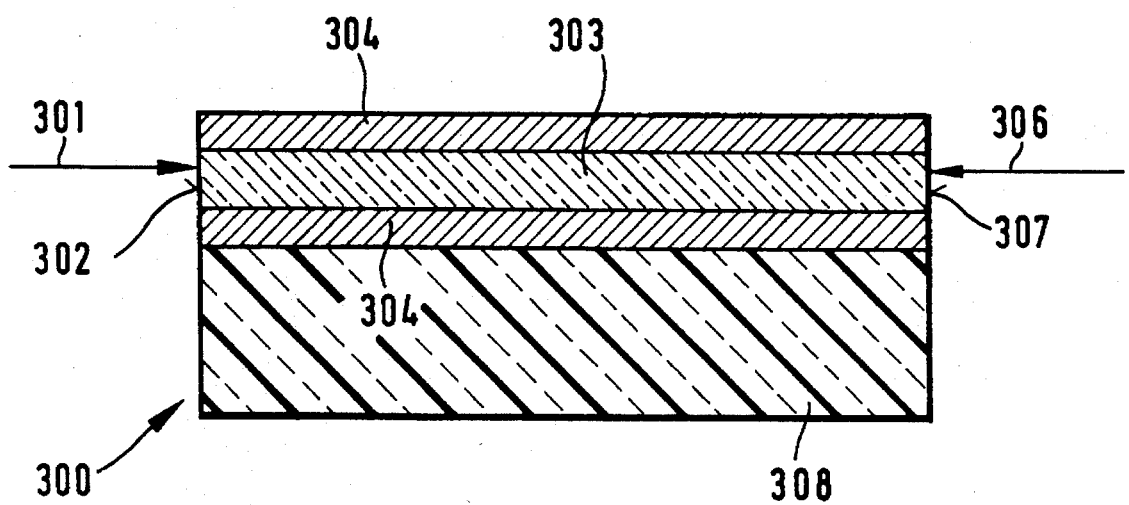
FIGS. 3a and 3b show an apparatus for modulating a lightwave.
Figure 3B:
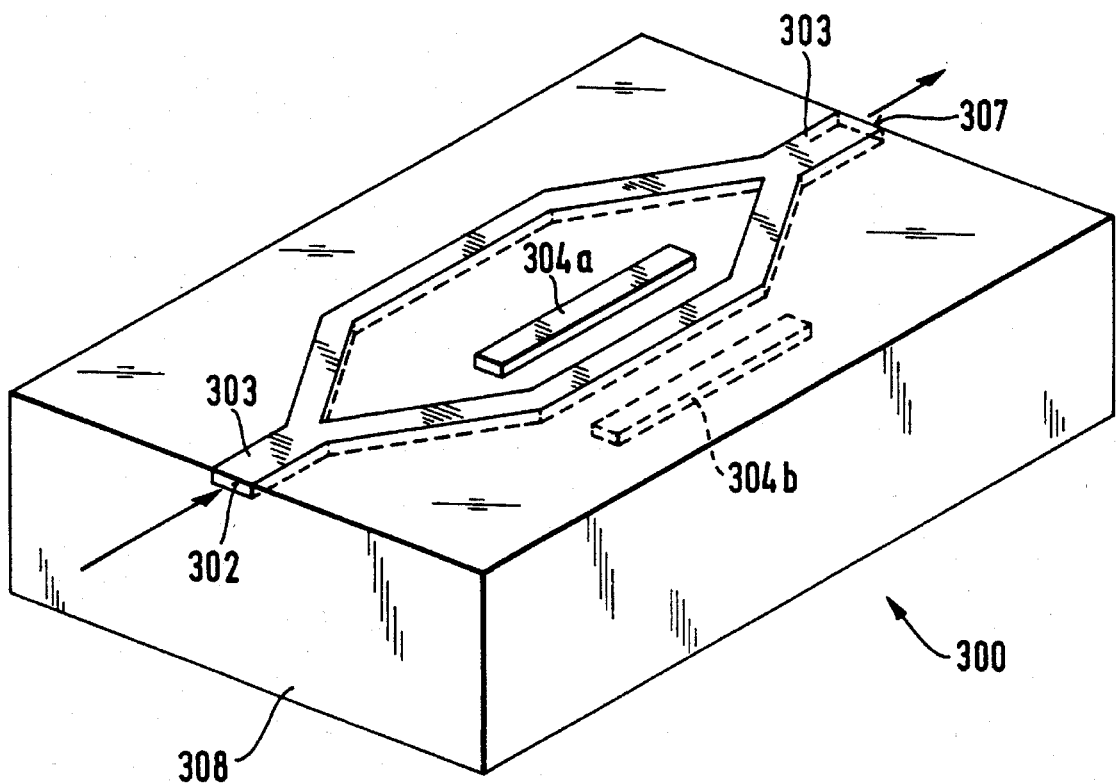

FIGS. 3a and 3b each show a component 300, by means of which the intensity of a lightwave can be modulated. The incident light 301 is launched into the active waveguide layer 303 via the end face 302, a prism (not shown) or a grating (not shown). The layer 303 is laterally structured as a Mach-Zehnder interferometer.

According to FIG. 3a which shows a component in cross section, two electrodes (304) are applied to either side of the waveguide 303 which rests on a transparent substrate. According to FIG. 3b, the electrodes 304 are accommodated with a lateral offset below and above one arm of the interferometer. The interferometer is arranged on a substrate 308.

When a voltage is applied to the electrodes 304, the refractive index in 303 and hence the phase velocity of the light in the particular arm of the interferometer change due to the linear electro-optical effect. This leads to an additive or subtractive superposition of the original wave and altered wave and to a modulation of the intensity of the light which is extracted via the end face 307.

Figure 4:
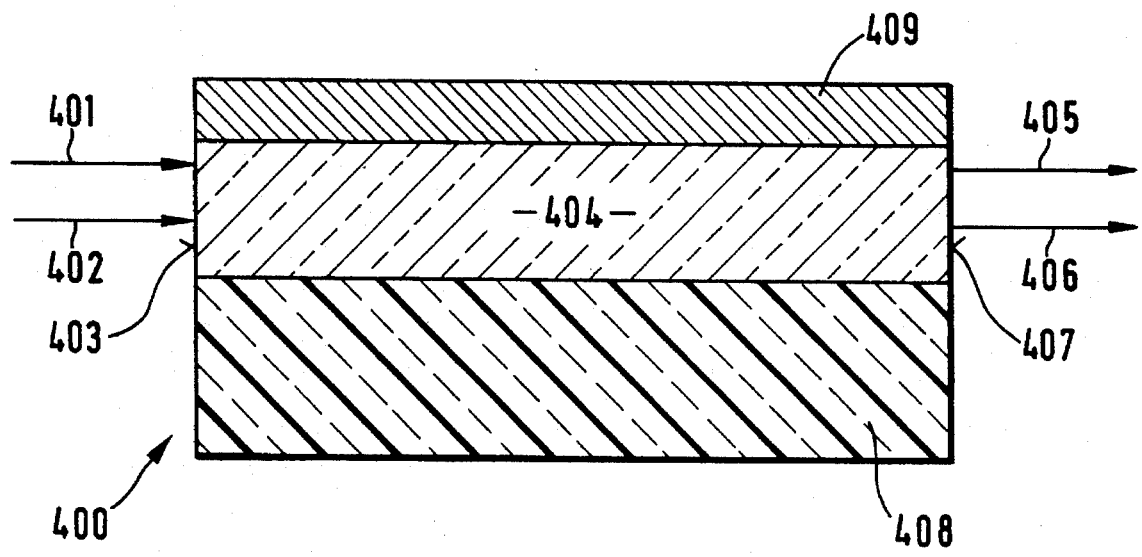
FIG. 4 shows an apparatus in which a first and second light beam interact.

FIG. 4 shows a component 400 in which an interaction between a first light beam 401 of frequency $\omega1$ and a second light beam 402 of frequency $\omega2$ occurs. In this case, new light beams, whose frequencies correspond to the sum and to the difference of $\omega3$ and $\omega4$, are generated. The beams of the frequencies $\omega1$ (401) and $\omega2$ (402) are launched via the end face 403 or via a prism (not shown) or a grating (not shown) into a waveguide structure 404 which is located on the substrate 408. The waveguide structure 404 can be covered with a protective layer 409.

The active layer 404 having waveguide function can be composed of NLO-active LB multilayers (analogously to FIG. 1); it can also have an additional NLO-inactive layer of high refractive index (analogously to FIG. 2).

The layer 404 can also be laterally structured for preparing a two-dimensional waveguide. The frequencies $\omega1$ and $\omega2$ are mixed in the layer 404 by the NLO interaction, i.e. a part of the launched intensity is converted into frequencies which correspond to the sum of the frequencies, and a part into frequencies which correspond to the difference between the frequencies $\omega1$ and $\omega2$. The light 405 and 406 which, inter alia, contains these frequencies can be extracted via the end face 407 or via a prism (not shown) or a grating (not shown).

The invention is explained in more detail by way of the following examples.

EXAMPLE 1

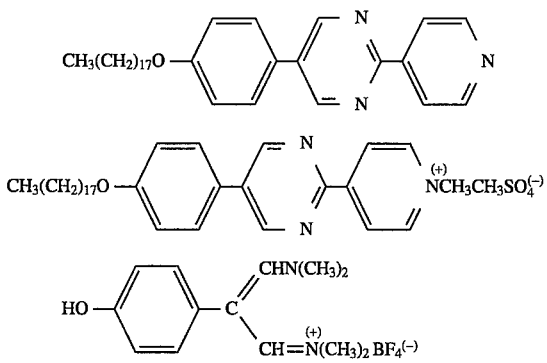

were admixed in 120 ml of methanol with 4.26 g of 4-pyridinecarbamidine hydrochloride and 13.5 ml of sodium methylate-methanol solution, and the mixture was stirred at room temperature for 30 minutes. After the addition of a further 9 ml of sodium methylate-methanol solution, the mixture was refluxed for 2 hours. The mixture was allowed to cool, 50 ml of water were added, and the yellow suspension was neutralized with hydrochloric acid. The precipitate was filtered off with suction, washed with water and methanol, and 4-(2-(4-pyridyl)-5-pyrimidinyl)phenol (B) was recrystallized from DMF.

1.5 g of B were heated to boiling with 0.61 g of potassium-carbonate in 400 ml of ethanol, until a clear yellow solution had formed, which was admixed with 2.17 g of molten octadecyl bromide. The mixture was refluxed for a further 20 hours, allowed to cool and stored overnight at −20° C. The precipitate of 5-(4-octadecyloxyphenyl)-2-(4-pyridyl)-pyrimidine (C) was recrystallized from ligroin.

Yield: 1.00 g (33%), melting point: 117° to 118° C., clearing point: 127° C. Absorption maximum in CHCl$_3$ 303 nm.

0.40 g (C) were heated in 50 ml of toluene until a clear solution had formed which was then admixed with 0.08 ml of dimethyl sulfate, the solution turning yellow in the process. The reaction mixture was refluxed for a further 2 hours, allowed to cool and stored overnight at −20° C. The precipitate of 1-methyl-4-(5-(4-octadecyloxyphenyl)- 2-pyrimidinyl)-pyridiniummethyl sulfate (D) was filtered off with suction, washed with toluene and recrystallized from ethanol.

Yield: 0.45 g (90%), melting point: 126° to 127° C., clearing point: 239° to 241° C., absorption maximum in CHCl$_3$ 376 nm.

EXAMPLE 2

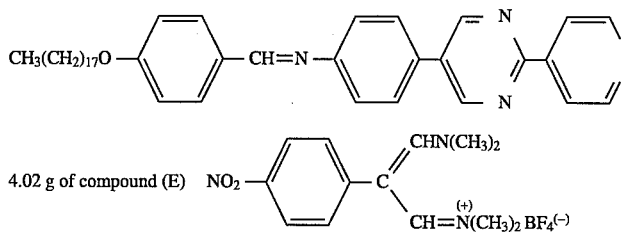

were stirred, similarly to Example 1, with 2.84 g of 4-pyridinecarbamidine hydrochloride and 9+6 ml of sodium methylate/methanol solution in 80 ml of methanol and heated. 5-(4-Nitrophenyl)-2-(4-pyridyl)-pyrimidine (F) was recrystallized from toluene.

A suspension of 1.39 g (F) in 50 ml of ethanol was admixed with 5.64 g of tin(II) chloride dihydrate and the mixture was heated to 70° C. for 40 min. It was then allowed to cool, 20 g of ice were added, and the pH was set to between 7 and 8 with sodium hydrogen carbonate solution. The precipitate was filtered off with suction, washed with water, dried in an oil pump vacuum and hot-extracted for 24 hours with 200 ml of anhydrous toluene under a protective gas atmosphere in a Soxhlet extractor. The precipitate of 4-(2-(4-pyridyl)-5-pyrimidinyl)aniline (G) precipitated from the toluene was filtered off with suction and dried in vacuo.

0.5 g (G) in 160 ml of toluene were refluxed with 1 g of p-octadecyloxybenzaldehyde and a trace of p-toluenesulfonic acid for 24 hours on a water separator. After cooling, compound (H) was recrystallized from petroleum ether.

Yield: 0.92 g (76%), melting point: 117° to 119° C., clearing point: 255° to 257° C., Absorption maximum in CHCl$_3$ 342 nm.

EXAMPLE 3

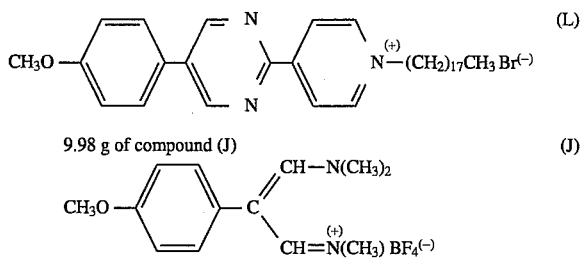

were reacted with 7.09 g of 4-pyridinecarbamidine hydrochloride and 22.5+15 ml of 2N sodium methylate/methanol solution in 150 ml of methanol. The 5-(4-methoxyphenyl)-2- (4-pyridyl) -pyrimidine (K) was recrystallized from 200 ml of toluene.

A solution of 1.32 g (K) in 50 ml of boiling toluene was admixed with 1.83 g of molten octadecyl bromide and the mixture was refluxed for 4 hours. The yellow solution was stored overnight at −20° C., the precipitate was filtered off with suction and washed with diethyl ether. Unreacted starting compound was leached by column chromatography on silica gel with toluene/ethyl acetate 1/1, and the product was eluted from the column with methylene chloride/methanol 10/1. After the solvent had been distilled off, (L) was recrystallized from toluene.

Yield: 1.05 g (35%), melting point: 158° to 160° C., clearing point: 194° to 196° C., Absorption maximum in CHCl$_3$ 370 nm.

EXAMPLE 4

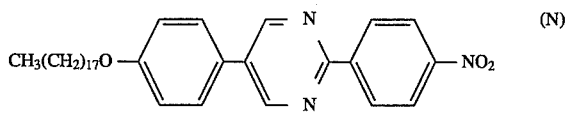

1.84 g of compound (A) were heated with 1.81 g of 4-nitrobenzamidine hydrochloride in 18 ml of pyridine to 80° C. for 5 hours. The mixture was then cooled and poured onto ice/concentrated sulfuric acid, the precipitate was filtered off with suction, washed with water, and 4-(2-nitrophenyl)- 5-pyrimidinyl)-phenol (M) was recrystallized from 1100 ml of toluene.

Similarly to Example 1, 0.59 g (M) was reacted with 0.73 g of octadecyl bromide and 0.21 g of potassium carbonate in 150 ml of ethanol. The crude product was purified by column chromatography (silica gel, methylene chloride) and recrystallization from petroleum ether, in order to isolate compound (N).

Yield: 0.45 g (41%), melting point: 116° C., clearing point: 225° to 226° C., Absorption maximum in $CHCl_3$ 335 nm.

EXAMPLE 5

Compound (D) was spread according to the Langmuir-Blodgett method onto a water surface and compressed. A slide made of glass was cleaned and rinsed with high-purity water; after this, the support surface was hydrophilic. The support was immersed through the monolayer on the air-water interface, no layer being transferred in the process, owing to the hydrophilic character of the substrate. The support was then removed through the interface, with a shear of 30 mN/m and at a velocity of 15 mm/min. At this point, a highly ordered monolayer was transferred to the slide.

The slide was mounted in a measuring system for frequency doubling according to the "Maker Fringes" method, and the intensity of the harmonic generated in the monolayer was measured at a wavelength of 1064 nm. This was used to determine values of 40 pm/V for $X^{(2)}_{zzz}$ and 10 pm/V for $X^{(2)}_{zxx}$ for the monolayer.

EXAMPLE 6

Compound (H) was spread according to the Langmuir-Blodgett method onto a water surface and compressed. A slide made of glass was cleaned and rinsed with high-purity water; after this, the support surface was hydrophilic. The support was immersed through the monolayer on the air-water interface, no layer being transferred in the process, owing to the hydrophilic character of the substrate. The support was then removed through the interface, with a shear of 20 mN/m and at a velocity of 2.5 m/min. At this point, a highly ordered monolayer was transferred to the slide.

The slide was mounted in a measuring system for frequency doubling according to the "Maker Fringes" method, and the intensity of the harmonic generated in the monolayer was measured at a wavelength of 1064 nm. This was used to determine values of 20 pm/V for $X^{(2)}_{zzz}$ and 5 pm/V for $X^{(2)}_{zxx}$ for the monolayer.

EXAMPLE 7

Compound (C) was spread according to the Langmuir-Blodgett method onto a water surface and compressed. A slide made of glass was cleaned and rinsed with high-purity water; after this, the support surface was hydrophilic. The support was immersed through the monolayer on the air-water interface, no layer being transferred in the process, owing to the hydrophilic character of the substrate. The support was then removed through the interface, with a shear of 20 mN/m and at a velocity of 2.5 mm/min. At this point, a highly ordered monolayer was transferred to the slide.

The slide was mounted in a measuring system for frequency doubling according to the "Maker Fringes" method, and the intensity of the harmonic generated in the monolayer was measured at a wavelength of 1064 nm. This was used to determine values of 5 pm/V for $X^{(2)}_{zzz}$ and 2.4 pm/V for $X^{(2)}_{zxx}$ for the monolayer.

EXAMPLE 8

The molecular hyperpolarizability of compound (C) was determined by measuring the hyper-Rayleigh scattering.

The hyper-Rayleigh effect was observed for the first time in 1965 and employed for determining the hyperpolarizabilities of NLO chromophores for the first time in 1991. A pulsed Nd:YAG laser is focussed onto a cuvette in which a solution of the chromophore to be examined has been placed. The solvent chosen is a compound, e.g. chloroform, whose hyperpolarizability β is known. Owing to local fluctuations of the orientation, a fraction of the elastically scattered light is emitted at twice the frequency; the intensity of the hyper-Rayleigh scattering is a quadratic function of the incident intensity and a linear function of the product of the concentration and β of the chromophore. The HRS-intensity is measured as a function of concentration, and by comparing the slope and the intercept of a plot of the HRS-intensity against the concentration, β can be determined.

Compound (C) was measured in chloroform according to this method, and a hyperpolarizability of $41 \times 10^{-30}$ esu at 1064 nm was found.

EXAMPLE 9

The molecular hyperpolarizability of compound (L) was determined by measuring the hyper-Rayleigh scattering in chloroform. This gave a value of $154 \times 10^{-30}$ esu.

EXAMPLE 10

Compound (N) was prepared as a solution with a concentration of 7 mg/l in chloroform and acetonitrile, and the absorption spectra were measured.

Based on the integrated absorption cross-section for the transition and the shift of the absorption wavelength between the two solvents it was possible to estimate a value of $0.8 \times 10^{-45}$ esu for the product of the hyperpolarizability β and the dipole moment μ at an application wavelength of 1064 nm.

11. 2,5-Bis(4-pyridyl)-pyrimidine (76)

The solution of 1.66 g (6 mmol) of 86[111] in 40 ml of anhydrous methanol was admixed with 1.42 g (9 mmol) of 4-pyridinecarbamidine hydrochloride[110] and 7.5 ml (15 mmol) of a 2N sodium methylate/methanol solution, and the mixture was stirred for 30 min at room temperature. After addition of a further 3 ml (6 mmol) of 2N sodium methylate/methanol solution, the mixture was refluxed for 2 h. Most of the solvent was then distilled off, and the residue was admixed with 50 ml of water. The precipitate was filtered off with suction, washed with water and recrystallized from 150 ml of toluene. Yield 1.01 g (72%); ivory-colored crystal powder, m.p. 235°–236° C.

IR (KBr): ν=3040 cm$^{-1}$, 1599, 1554, 1526, 1437, 1419, 1329, 1232, 825, 786, 716. - UV (CH$_3$CN): λ$_{max}$ (1 g ε)= 271 nm (4.475), 320 (sh, 3.154). - UV (CHCl$_3$): λ$_{max}$ (1 g ε) =273 nm (4.468), 320 (sh, 3.171). -$^1$H NMR ([D$_6$]DMSO): δ =7.81 (d, 2H, 5-(4-pyridyl)-NCHCH), 8.23 (d, 2H, 2-(4-pyridyl)-NCHCH), 8.60–8.78 (m, NCHCH), 9.29 (s, 2H, pyrimidine-H). -MS (70 eV):m/z (%)=234 (100) [M$^+$], 103 (40). - TLC (CH$_2$Cl$_2$/methanol 10/1): R$_f$=0.46.

| C$_{14}$H$_{10}$N$_4$ | Calc. | C 71.78 | H 4.30 | N 23.92 |
|---|---|---|---|---|
| (234.3) | Found | C 71.77 | H 4.21 | N 23.83 |

12. 5-(4-Methoxyphenyl)-2-(4-nitrophenyl)-pyrimidine (80)

The suspension of 1.92 g (6 mmol) of 77$^{130}$ in 18 ml of anhydrous pyridine was admixed with 1.81 g (9 mmol) of 4-nitrobenzamidine hydrochloride$^{131}$, and the mixture was heated to 80° C. for 5 h. Then the cooled reaction mixture was poured onto ice/conc. sulfuric acid (120 g/22.2 ml), the precipitate was filtered off with suction, washed with water and recrystallized from 150 ml of toluene. Yield 1.58 g (86%); fluorescing yellow needles, m.p. 243°–244° C.

IR (KBr): ν=1608 cm$^{-1}$, 1601, 1543, 1520, 1431, 1347, 1261, 743. - UV (CH$_3$CN): λ$_{max}$ (1 g ε)=256 nm (4.151), 330 (4.348). -UV (CHCl$_3$): λ$_{max}$ (1 g ε)=258 nm (4.232), 333 (4.376). -$^1$H-NMR ([D$_6$]DMSO): δ=3.75 (s, 3H, OCH$_3$), 6.98 (d, 2H, CCHCHCOCH$_3$), 7.68 (d, 2H, CCHCHCOCH$_3$), 8.30 (d, 2H, CCHCHCNO$_2$), 8.50 (d, 2H, CCHCHCNO$_2$), 9.05 (s, 2H, pyrimidine-H). -$^1$H NMR (CF$_3$COOH): δ=4.00 (s, 3H, OCH$_3$), 7.23 (d, 2H, CCHCHCOCH$_3$), 7.78 (d, 2H, CCHCHCOCH$_3$), 8.55 (s, 4H, nitrophenyl-H), 9.53 (s, 2H, pyrimidine-H). -MS (70 eV): m/z (%)=307 (100) [M$^+$], 292 (7) [M$^+$- OCH$_3$], 277 (12) [M$^+$-NO], 261 (11) [M$^+$- NO$_2$]. - TLC (toluene/AcOEt 4/1): R$_f$=0.76.

| C$_{17}$H$_{13}$N$_3$O$_3$ | Calc. | C 66.44 | H 4.26 | N 13.67 |
|---|---|---|---|---|
| (307.3) | Found | C 66.59 | H 4.33 | N 13.64 |

13. 2-(4-Methoxyphenyl)-5-(4-nitrophenyl)-pyrimidine (81)

As described under 12, from 1.93 g (6 mmol) of 78$^{130}$ and 1.70 g (9 mmol) of 4-methoxybenzamidine hydrochloride$^{132}$ in 18 ml of anhydrous pyridine. Recrystallization was carried out from 130 ml of toluene. Yield 1.55 g (84%); small felted, pale yellow needles, m.p. 213°–214° C.

IR (KBr): ν=1615 cm$^{-1}$, 1599, 1581, 1521, 1433, 1346, 1263, 1169, 798. - UV (CH$_3$CN): λ$_{max}$ (log ε)=262 nm (4.079), 329 (4.504). - UV (CHCl$_3$): λ$_{max}$ (log ε)=266 nm (4.148), 336 (4.470). - $^1$H NMR {[D$_6$]DMSO): δ=3.80 (s, 3H, OCH$_3$), 7.04 (d, 2H, CCHCHCOCH$_3$), 8.05 (d, 2H, CCHCHCNO$_2$), 8.25–8.45 (m, 4H, CCHCHCOCH$_3$ and CCHCHCNO$_2$) 9.15 (s, 2H, pyrimidine-H). - MS (70 eV): m/z (%)=307 (100) [M$^+$], 292 (2) [M$^+$- OCH$_3$], 277 (13) [M$^+$- NO]. - TLC (toluene/AcOEt 4/1): R$_f$=0.76.

| C$_{17}$H$_{13}$N$_3$O$_3$ | Calc. | C 66.44 | H 4.26 | N 13.67 |
|---|---|---|---|---|
| (307.3) | Found | C 66.34 | H 4.35 | N 13.74 |

14. 4-[2- (4-Nitrophenyl) -5-pyrimidinyl)-phenol (82)

As described under 12, from 1.84 g (6 mmol) of 79$^{133}$ and 1.81 g (9 mmol) of 4-nitrobenzamidine hydrochloride$^{131}$ in 18 ml of anhydrous pyridine. Recrystallization was carried out from 1100 ml of toluene. Yield 0.76 g (43%); yellow needles, m.p. 305°–306° C.

IR (KBr): ν=3426 cm$^{-1}$, 1611, 1589, 1545, 1522, 1507, 1430, 1355, 1339, 1275, 1188, 841, 744. -UV (CH$_3$CN): λ$_{max}$ (log ε)=256 nm (4.221), 332 (4.404), 430 (sh, 2.817). -UV (CHCl$_3$), qual.: λ$_{max}$=255 nm, 324. -UV (DMSO): λ$_{max}$ (log ε)=350 nm (4.317), 440 (sh, 2.719). - UV (DMSO+ KO$^t$Bu) , qual.: λ$_{max}$=417 nm, 537. - UV (CF$_3$COOH): λ$_{max}$ (log ε)=278 nm (4.237), 324 (4.273), 350 (sh, 4.238). $^1$H NMR ([D$_6$]DMSO): δ=6.89 (d, 2H, CCHCHCOH), 7.70 (d, 2H, CCHCHCOH) , 8.33 (d, 2H, CCHCHCNO$_2$), 8.60 (d, - 2H, CCHCCNO$_2$), 9.18 (s, 2H, pyrimidinyl-H), 9.80 (s, broad, 1H, OH). - MS (70 eV): m/z (%)=293 (100) [M$^+$], 263 (19) [M$^+$–NO], 247 (23) [M$^+$–NO$_2$].

| C$_{16}$H$_{11}$N$_3$O$_3$ | Calc. | C 65.53 | H 3.78 | N 14.33 |
|---|---|---|---|---|
| (293.3) | Found | C 65.85 | H 3.83 | N 14.18 |

15. 5-(4-Methoxyphenyl)-2-(4-pyridyl)-pyrimidine (87)

As described under 11, from 9.98 g (30 mmol) of 77$^{130}$, 7.09 g (45 mmol) of 4-pyridinecarbimidine hydrochloride$^{116}$ and 22.5+15 ml of 2N sodium methylate/methanol solution in 150 ml of anhydrous methanol. Recrystallization was carried out from 200 ml of toluene. Yield 4.91 g (62%); colorless platelets, m.p. 193° C.

IR (KBr): ν=1609 cm$^{-1}$, 1598, 1578, 1520, 1433, 1294, 1255, 1183, 836, 786, 688. - UV (CH$_3$CN) , qual.: λ$_{max}$= 227 nm, 300. - UV (CHCl$_3$) , qual.: λ$_{max}$=299 nm. $^1$H NMR ([D$_6$]DMSO): δ=3.84 (s, 3H, OCH$_3$), 7.13 (d, J=8.7 Hz, 2H, CCHCHCOCH$_3$), 7.87 (d, J=8.7 Hz, 2H, CCHCHCOCH$_3$), 8.30 (d, J=6.1 Hz, 2H, NCHCH), 8.78 (d, J=6.1 Hz, 2H, NCHCH), 9.30 (s, 2H, pyrimidine-H) . - $^{13}$C NMR ( [D$_6$]DMSO): δ=55.26 (CH$_3$) , 114.78 (methoxyphenyl C-3 and C-5) , 121.19 (pyridyl C-3 and C-5), 125.42 (methoxyphenyl C-1), 128.15 (methoxyphenyl C-2 and C-6), 131.97 (pyrimidine C-5), 143.93 (pyridyl C-4), 150.46 (pyridyl C-2 and C-6), 154.77 (pyrimidine C-4 and C-6), 159.46 (pyrimidine C-2), 160.14 (methoxyphenyl C-4). - MS (70 eV): m/z (%)=263 (100) [M$^+$], 248 (31) [M$^+$ - CH$_3$], 220 (13) [M$^+$–COCH$_3$]. - TLC (CH$_2$Cl$_2$/methanol 10/1): R$_f$=0.57.

| C$_{16}$H$_{13}$N$_3$O | Calc. | C 72.99 | H 4.98 | N 15.96 |
|---|---|---|---|---|
| (263.3) | Found | C 72.98 | H 5.10 | N 15.89 |

16. 5-(4-Nitrophenyl)-2-(4-pyridyl)-pyrimidine (88)

As described under 11, from 4.02 g (12 mmol) of 78$^{130}$, 2.84 g (18 mmol) of 4-pyridinecarbamidine hydrochloride$^{116}$ and 9+6 ml of 2N sodium methylate/methanol solution in 80 ml of anhydrous methanol. Recrystallization was carried out from 500 ml of toluene. Yield 2.80 g (84%); light-ocher needles, m.p. 276°–277° C.

IR (KBr): ν=1599 cm⁻¹, 1520, 1435, 1356, 1340, 857, 850, 786, 662. - UV (CH₃CN): λ$_{max}$ (log ε)=297 nm (4.465). -UV (CHCl₃): λ$_{max}$ (log ε)=297 nm (4.453) . - ¹H NMR ([D₆]DMSO): δ=8.07–8.40 (m, 6H, NCHCH and nitrophenyl-H), 8.78 (d, 2H, NCHCH), 9.35 (s, 2H, pyrimidine-H). -MS (70 eV):m/z (%)=278 (100) [M⁺], 248 (28) [M⁺–NO], 232 (5) [M⁺–NO₂]. –TLC (AcOEt): R$_f$=0.53.

17. 4-[2-(4-Pyridyl)-5-pyrimidinyl]-phenol (89)

The solution of 5.51 g (18 mmol) of 79[133] in 120 ml of anhydrous methanol was admixed with 4.26 g (27 mmol) of 4-pyridinecarbamidine hydrochloride[110] and 13.5 ml of 2N sodium methylate/methanol solution and the mixture was stirred at room temperature for 30 min. After addition of a further 9 ml of 2N sodium methylate/methanol solution, the mixture was refluxed for 2 h. It was allowed to cool, 50 ml of water were added, and the yellow suspension was neutralized with concentrated hydrochloric acid, becoming colorless in the process. The precipitate was filtered off with suction, washed with water and methanol and recrystallized from 150 ml of DMF. Yield 3.16 g (70%); faintly yellowish needles, m.p. >350° C.

IR (KBr): ν=1608 cm⁻¹, 1585, 1520, 1430, 1283, 1254, 1216, 1174, 831, 783, 697. -UV (CH₃CN), qual.: λ$_{max}$=301 nm, 370 (sh). -UV (DMSO): λ$_{max}$ (log ε)=316 nm (4.350), 375 (sh, 2.964). - UV (DMSO+KOᵗBu), qual.: λ$_{max}$=360 nm, 458. - ¹H NMR ([D₆]DMSO): δ=6.95 (d, J=8.7 Hz, 2H, CCHCHCOH), 7.75 (d, 2H, J=8.7 Hz, 2H, CCHCHCOH), 8.29 (d, J=6.1 Hz, 2H, NCHCH), 8.78 (d, J=6.1 Hz, 2H, NCHCH), 9.26 (s, 2H, pyrimidinyl-H), 9.89 (s, 1H, OH). - ¹³C NMR ([D₆]DMSO): δ=116.13 (phenol C-2 and C-6), 121.14 (pyridyl C-3 and C-5), 123.72 (phenol C-4), 128.13 (phenol C-3 and C-5), 132.27 (pyrimidinyl C-5), 143.97 (pyridyl C-4), 150.44 (pyridyl C-2 and C-6), 154.48 (pyrimidinyl C-4 and C-6), 158.58 (phenol C-1), 159.16 (pyrimidinyl C-2). - MS (70 eV): m/z (%)=249 (100) [M⁺], 118 (34). - TLC (CH₂Cl₂/methanol 10/1): R$_f$=0.91.

| C₁₅H₁₁N₃O (249.3) | Calc. Found | C 72.28 C 72.71 | H 4.45 H 4.56 | N 16.86 N 16.67 |
|---|---|---|---|---|

18. 2-(4-Methoxyphenyl)-5-(4-pyridyl)-pyrimidine (90)

As described under 11, from 3.31 g (12 mmol) of 86[111], 3.36 g (18 mmol) of 4-methoxybenzamidine hydrochloride[132] and 15+6 ml of 2N sodium methylate/methanol solution in 60 ml of anhydrous methanol. Recrystallization was carried out from 100 ml of toluene. Yield 2.58 g (82%); colorless platelets, m.p. 183° C.

IR (KBr): ν=1609 cm⁻¹ (sh), 1598, 1583, 1556, 1433, 1256, 1246, 1168, 1022, 822. - UV (CH₃CN): λ$_{max}$ (log ε)= 307 nm (4.465). UV (CHCl₃): λ$_{max}$ (log ε)=316 nm (4.471). -¹H NMR ([D₆]DMSO): δ=3.82 (s, 3H, OCH₃), 7.05 (d, 2H, CCHCHCOCH₃), 7.83 (d, 2H, NCHCH), 8.35 (d, 2H, CCHCHCOCH₃), 8.68 (d, 2H, NCHCH), 9.20 (s, 2H, pyrimidine-H). - MS (70 eV): m/z (%)=263 (100) [M⁺], 248 (12) [M⁺ - CH₃]. - TLC (CH₂Cl₂/methanol 10/1): R$_f$= 0.54.

19. 2-(4-Nitrophenyl)-5-(4-pyridyl)-pyrimidine (91)

As described under 11, from 4.97 g (18 mmol) of 86[111], 5.44 g (27 mmol) of 4-nitrobenzamidine hydrochloride[131] and 22.5+9 ml of 2N sodium methylate/methanol solution in 120 ml of anhydrous methanol. Recrystallization was carried out from 200 ml of toluene. Yield 3.03 g (60%); light beige needles, m.p. 225°–226° C.

IR (KBr): ν=1615 cm⁻¹ (sh), 1601, 1559, 1523, 1433, 1343, 823, 744. - UV (CH₃CN): λ$_{max}$ (log ε)=252 nm (4.004), 302 (4.496). - UV (CHCl₃): λ$_{max}$ (log ε)= 250 nm (sh, 4.004), 302 (4.541). - ¹H NMR ([D₆]DMSO): δ=7.85 (d, 2H, NCHCH), 8.29 (d, 2H, CCHCHCNO₂), 8.59 (d, 2H, CCHCHCNO₂), 8.66 (d, 2H, NCHCH), 9.33 (s, 2H, pyrimidine-H). - MS (70 eV): m/z (%)=278 (100) [M⁺], 248 (22) [M⁺–NO], 232 (33) [M⁺- NO₂]. - TLC (AcOEt): R$_f$=0.35.

| C₁₅H₁₀N₄O₂ (278.3) | Calc. Found | C 64.74 C 64.48 | H 3.62 H 3.72 | N 20.13 N 20.09 |
|---|---|---|---|---|

20. 4-[2-(4-Pyridyl)-5-pyrimidinyl]-aniline (97)

The suspension of 1.39 g (5 mmol) of 88 in 50 ml of anhydrous ethanol was admixed with 5.64 g (25 mmol) of tin(II) chloride dihydrate and the mixture was heated to 70° C. for 40 min. It was then allowed to cool, 20 g of ice were added, and the pH was set to between 7 and 8 by adding 5 percent strength aqueous sodium hydrogen carbonate solution (approximately 100 ml). The precipitate was filtered off with suction, washed with water, dried in an oil pump vacuum and hot-extracted for 24 hours with 200 ml of anhydrous toluene under a protective gas atmosphere in a Soxhlet extractor. The precipitate produced from the toluene extracts was filtered off with suction and dried in vacuo. Yield 1.08 g (87%); pale yellow powder, m.p. 315°–317° C.

IR (KBr): ν=3439 cm⁻¹, 3322, 3188, 1643, 1610, 1602, 1572, 1527, 1435, 1317, 1189, 831, 782, 693. - UV (CH₃CN): λ$_{max}$ (log ε)=241 nm (4.253), 310 (sh, 4.195), 341 (4.327). -UV (CHCl₃): λ$_{max}$ (log ε)=240 nm (4.264), 300 (sh, 4.213), 334 (4.320). -UV (CF₃COOH): λ$_{max}$ (log ε) =280 nm (sh, 4.271), 297 (4.319). - UV (DMSO): λ$_{max}$ (log ε)=310 nm (sh, 3.967), 367 (4.378). - UV (DMSO+ KOᵗBu): λ$_{max}$ (log ε)=300 nm (3.963), 368 (4.281), 450 (sh, 3.571). - ¹H NMR ([D₆]DMSO): δ=5.30 (s, broad, 2H, NH₂), 6.71 (d, 2H, CCHCHCNH₂), 7.55 (d, 2H, CCHCHCNH₂), 8.22 (d, 2H, NCHCH), 8.72 (d, 2H, NCHCH), 9.10 (s, 2H, pyrimidinyl-H) . - ¹H NMR (CF₃COOH): δ=7.77 (d, 2H, CCHCHCNH₂), 7.96 (d, 2H, CCHCHCNH₂), 9.03 (s, 4H, pyridyl-H), 9.45 (s, 2H, pyrimidinyl-H). -MS (70 eV): m/z (%)= 248 (100) [M⁺], 117 (28) . - TLC (CH₂Cl₂/methanol 10/1): R$_f$=0.55.

21. 4-[5-(4-Pyridyl)-2-pyrimidinyl]-aniline (98)

As described under 20, from 1.39 g (5 mmol) of 91 and 5.64 g (25 mmol) of tin (II) chloride dihydrate. Yield 0.92 g (74%); pale yellow powder, m.p. 293°–294° C.

IR (KBr): ν= 3375 cm⁻¹, 3329, 3208, 1643, 1599, 1579, 1553, 1433, 1298, 1173, 827, 798. - UV (CH₃CN): λ$_{max}$ (log ε)=340 nm (4.533). - UV (CHCl₃): λ$_{max}$ (log ε)=337 nm (4.492). - UV (CF₃COOH): λ$_{max}$ (log ε)=275 nm (sh, 4.369), 296 (4.428), 380 (sh, 2.336), 440 (sh, 2.084). - UV (DMSO): λ$_{max}$ (log ε)=305 nm (sh, 3.868), 363 (4.557). - UV (DMSO+KOᵗBu): λ$_{max}$ (log ε)=359 nm (4.400), 430 (sh, 3.728). - ¹H NMR ([D₆]DMSO): δ=5.63 (s, broad, 2H, NH₂), 6.64 (d, 2H, CCHCHCNH₂), 7.78 (d, 2H, NCHCH), 8.13 (d, 2H, CCHCHCNH₂), 8.64 (d, 2H, NCHCH), 9.10 (s, 2H, pyrimidinyl-H) . - ¹H NMR (CF₃COOH): δ=7.87 (d, 2H, CCHCHCNH₂), 8.53–8.64 (m, 4H, CCHCHCNH₂ and NCHCH), 9.04 (d, 2H, NCHCH), 9.80 (s, 2H, pyrimidinyl-H). -MS (70 eV): m/z (%)=248 (100) [M⁺], 124 (5) [M²⁺], 118 (33). - TLC (CH₂Cl₂/methanol 10/1): R$_f$=0.57.

| | | | |
|---|---|---|---|
| C$_{15}$H$_{12}$N$_4$ | Calc. | C 72.56 | H 4.87 | N 22.57 |
| (248.3) | Found | C 72.35 | H 4.92 | N 22.45 |

22. 4-[2-(4-Pyridyl)-5-pyrimidinyl]-phenylhydrazine (100)

0.74 g (3 mmol) of 97, dissolved in 30 ml of 75 percent strength hydrochloric acid, was admixed dropwise at 20° C. with a solution of 0.228 g (3.3 mmol) of sodium nitrite in a little water. The diazonium salt solution thus prepared was added dropwise at −10° C., using a dropping pipette, to a solution of 1.49 g (6.6 mmol) of tin(II) chloride dihydrate in 1.5 ml of concentrated hydrochloric acid. In doing so, the internal temperature was kept at −10° C.±2° C. by means of a cold bath. The orange precipitate produced was filtered off with suction and suspended in 60 ml of ice water, the greater part dissolving in the process. The mixture was neutralized with 2N aqueous sodium hydroxide, a flocculent, yellow precipitate being formed which was filtered off with suction, washed with water and methanol, dried in vacuo and hot-extracted for 24 h with 200 ml of anhydrous toluene under protective gas in a Soxhlet extractor. The precipitate produced from the extracts was filtered off with suction and dried in vacuo. Yield 0.55 g (70%); flocculent, small bright yellow needles, m.p. 251°–253° C. (decomp.).

IR (KBr): ν=3249 cm$^{-1}$, 1610, 1601, 1525, 1434, 1408, 1303, 1195, 828, 783. -UV (CH$_3$CN): λ$_{max}$ (log ε)=300 nm (sh, 4.094), 346 (4.324) . - UV (CHCl$_3$): λ$_{max}$ (log ε)= 300 nm (sh, 4.186), 334 (4.259). - UV (DMSO): λ$_{max}$ (log ε) =305 nm (sh, 3.912), 372 (4.317). - UV (CF$_3$COOH): λ$_{max}$ (log ε)=344 nm (broad, 4.141). - UV (DMSO+KO$^t$Bu), qual.: λ$_{max}$=346 nm, 462. - $^1$H NMR ([D$_6$]DMSO): δ=4.02 (s, broad, 2H, NH$_2$), 8.90 (d, 2H, CCHCHCNHNH$_2$), 7.03 (s, 1H, NH), 7.63 (d, 2H, CCHCHCNHNH$_2$), 8.21 (d, 2H, NCHCH), 8.69 (d, 2H, NCHCH), 9.13 (s, 2H, pyrimidinyl-H). -$^1$H NMR ([D$_6$]DMSO): δ=7.33 (d, 2H, CCHCHCNHNH$_2$), 7.85 (d, 2H, CCHCHCNHNH$_2$), 9.00 (s, 4H, pyridyl-H), 9.45 (s, 2H, pyrimidinyl-H). - MS (70 eV): m/z (%)=263 (100) [M$^+$], 247 (52) [M$^+$ - NH$_2$]. - TLC (CH$_2$Cl$_2$/methanol 10/1): R$_f$=0.42.

23. 4-[5-(4-Methoxyphenyl)-2-pyrimidinyl]-1-methylpyridinium methyl sulfate (101)

0.6 g (2.28 mmol) of 87 was heated in 50 ml of toluene until a clear solution had formed, which was then admixed with 0.23 ml (2.43 mmol) of dimethyl sulfate, a flocculent yellow precipitate being formed at once. After the mixture had been refluxed for 1 more hour, the precipitate formed was hot- filtered with suction and washed with toluene. Yield 0.77 g (87%); flocculent yellow powder, m.p. 152° C. (decomp.).

IR (KBr): ν=1638 cm$^{-1}$, 1608, 1535, 1519, 1433, 1256, 1187, 1010, 837, 792, 761. - UV (CH$_3$CN): λ$_{max}$ (log ε)= 243 nm (4.248), 352 (4.272). - UV (CHCl$_3$), qual.: λ$_{max}$= 250 nm, 369. - $^1$H NMR ([D$_6$]DMSO): δ=3.38 (s, 3H, methyl sulfate) , 3.85 (s, 3H, OCH$_3$), 4.43 (s, 3H, N$^+$CH$_3$), 7.15 (d, J=8.7 Hz, 2H, CCHCHCOCH$_3$), 7.94 (d, J=8.7 Hz, 2H, CCHCHCOCH$_3$), 8.89 (d, J=6.8 Hz, 2H, N$^+$CHCH), 9.12 (d, J =6.8 Hz, 2H, N$^+$CHCH), 9.44 (s, 2H, pyrimidinyl-H). - $^{13}$C NMR ([D$_6$]DMSO): δ=47.68 (q, N$^+$CH$_3$), 52.69 (q, H$_3$CSO$_4$$^-$), 55.35 (q, OCH$_3$), 114.91 (d, methoxyphenyl C-3 and C-5), 124.66 (d, pyridinium C-3 and C-5), 124.77 (s, methoxyphenyl C-1), 128.57 (dimethoxyphenyl C-2 and C-6), 133.26 (s, pyrimidinyl C-5) , 146.41 (d, pyridinium C-2 and C-6), 150.71 (s, pyridinium C-4), 155.07 (d, pyrimidinyl C-4 and C-6), 156.46 (s, pyrimidinyl C-2), 160.64 (s, pyridinium C-4). - TLC (CH$_2$Cl$_2$/methanol 1/1): R$_f$=0.31.

| | | | | |
|---|---|---|---|---|
| C$_{18}$H$_{19}$N$_3$O$_5$S | Calc. | C 55.52 | H 4.92 | N 10.79 |
| (389.4) | Found | C 55.82 | H 4.89 | N 10.79 |

24. 1-Methyl-4-[5-(4-nitrophenyl)-2-pyrimidinyl)-pyridinium methyl sulfate (102)

As described under 23, from 0.556 g (2 mmol) of 88 and 0.2 ml (2.1 mmol) of dimethyl sulfate in 100 ml of toluene. Yield 0.78 g (96%); ivory-colored powder, m.p. 240°–242° C.

IR (KBr): ν=3058 cm$^{-1}$, 1641, 1602, 1520, 1434, 1353, 1250, 1230, 1010, 857, 753. -UV (CH$_3$CN): λ$_{max}$ (log ε)=308 nm (4.514). - UV (CHCl$_3$): λ$_{max}$ (log ε)=309 nm (4.440). - $^1$H NMR ([D$_6$]DMSO): δ=3.34 (s, 3H, methyl sulfate), 4.40 (s, 3H, N$^+$CH$_3$), 8.20 (d, 2H, CCHCHCNO$_2$), 8.37 (d, 2H, CCHCHCNO$_2$), 8.87 (s, 2H, N*CHCH), 9.10 (d, 2H, N$^+$CHCH), 9.50 (s, 2H, pyrimidinyl-H).

| | | | | |
|---|---|---|---|---|
| C$_{17}$H$_{16}$N$_4$O$_6$S | Calc. | C 50.49 | H 3.99 | N 13.85 |
| (404.4) | Found | c 50.80 | H 4.04 | N 13.70 |

25. 4-[5-(4-Hydroxyphenyl)-2-pyrimidinyl]-1-methylpyridinium tetrafluoroborate (103)

The suspension of 1.00 g (4 mmol) of finely powdered 89 in 400 ml of boiling toluene was admixed with 0.40 ml (4.2 mmol) of dimethyl sulfate and the mixture was refluxed for 20 h. After cooling, the precipitate was filtered off with suction, washed with toluene and, together with 5 g (45.5 mmol) of sodium tetrafluoroborate, was heated to boiling in 100 ml of water and hot-filtered. Upon cooling, the filtrate produced a flocculent, yellow precipitate which was filtered off with suction, washed with water and recrystallized from 50 ml of water. Yield 0.79 g (56%); yellow powder, m.p. >350° C.

IR (KBr): δ=3121 cm$^{-1}$ (broad), 1639, 1610, 1587, 1533, 1520, 1432, 1278, 1182, 1084, 841, 792. -UV (CH$_3$CN): λ$_{max}$ (log ε)=243 nm (4.180), 355 (4.218). - UV (DMSO): λ$_{max}$ (log ε)=368 nm (4.237). - UV (DMSO+KO$^t$Bu), qual.: λ$_{max}$ =340 nm (sh), 365, 594 (broad). - $^1$H NMR ([D$_6$] DMSO): δ= 4.42 (s, 3H, N$^+$CH$_3$), 6.97 (d, J=8.6 Hz, 2H, CCHCHCOH), 7.83 (d, J=8.6 Hz, 2H, CCHCHCOH), 8.88 (d, J=6.8 Hz, 2H, N$^+$CHCH), 9.11 (d, J=8.6 Hz, 2H, N$^+$CHCH), 9.40 (s, 2H, pyrimidinyl-H), 10.01 (s, 1H, OH) . - $^{13}$C NMR ([D$_6$]DMSO): δ=47.65 (q, N$^+$CH$_3$), 116.29 (d, hydroxyphenyl C-3 and C-5), 123.07 (s, hydroxyphenyl C-1), 124.60 (d, pyridinium C-3 and C-5), 128.57 (d, hydroxyphenyl C-2 and C-6), 133.56 (s, pyrimidinyl C-5), 146.32 (d, pyrimidinyl C-4 and C-6) , 150.77 (s, pyridinium C-4), 154.73 (d, pyridinium C-2 and C-6) , 156.12 (s, pyrimidinyl C-2), 159.18 ( s, hydroxyphenyl C-4).

| | | | | |
|---|---|---|---|---|
| C$_{16}$H$_{14}$BF$_4$N$_3$O | Calc. | C 54.7 | H 4.02 | N 11.97 |
| (351.1) | Found | C 55.26 | H 4.13 | N 11.93 |

26. 4-[2-(4-Methoxyphenyl)-5-pyrimidinyl]-1-methylpyridinium methyl sulfate (104)

As described under 23, from 0.66 g (2.5 mmol) of 90 and 0.25 ml (2.6 mmol) of dimethyl sulfate in 50 ml of toluene.

Yield 0.80 g (82%); colorless flocculent powder, m.p. 230° C. (decomp.).

IR (KBr): ν=1645 cm$^{-1}$, 1608, 1581, 1437, 1253, 1166, 1011, 845, 800, 744. - UV (CH$_3$CN): λ$_{max}$ (log ε)=248 nm (4.163), 265 (sh, 4.036), 349 (4.491). -UV (CHCl$_3$): λ$_{max}$ (log ε)=258 nm (4.215), 270 (sh, 4.138), 372 (4.465). -$^1$H NMR ([D$_6$]DMSO): δ=3.36 (s, 3H, methyl sulfate), 3.83 (s, 3H, OCH$_3$), 4.35 (s, 3H, N$^+$CH$_3$), 7.05 (d, 2H, CCHHCH-COCH$_3$), 8.38 (d, 2H, CCHCHCOCH$_3$), 8.58 (d, 2H, N$^+$CHCH), 9.01 (d, 2H, N$^+$CHCH), 9.42 (s, 2H, pyrimidinyl-H).

| C$_{18}$H$_{19}$N$_3$O$_5$S | Calc. | C 55.52 | H 4.92 | N 10.79 |
|---|---|---|---|---|
| (389.4) | Found | C 55.26 | H 4.63 | N 10.60 |

27. 1-Methyl-4-[2-(4-nitrophenyl)-5-pyrimidinyl]-pyridinium methyl sulfate (105)

As described under 23, from 0.56 g (2 mmol) of 91 and 0.20 ml (2.1 mmol) of dimethyl sulfate in 50 ml of toluene. Yield 0.62 g (77%); colorless powder, m.p. 311°–313° C. (decomp.).

IR (KBr): ν=1646 cm$^{-1}$, 1607, 1583, 1523, 1440, 1355, 1341, 1250, 1014, 856, 743. -UV (CH$_3$CN): λ$_{max}$ (log ε)= 270 nm (sh, 4.110), 313 (4.609). -UV (CHCl$_3$), qual.: λ$_{max}$ =270 (sh), 317 nm. - $^1$H NMR ([D$_6$]DMSO): δ=3.35 (s, 3H, methyl sulfate), 4.37 (s, 3H, N$^+$CH$_3$), 8.36 (d, 2H, CCH-CHCNO$_2$), 8.60–8.75 (m, 4H, CCHCHCNO$_2$ and N$^+$CHCH), 9.08 (d, 2H, N$^+$CHCH), 9.60 (s, 2H, pyrimidinyl-H).

| C$_{17}$H$_{16}$N$_4$O$_6$S | Calc. | C 50.49 | H 3.99 | N 13.85 |
|---|---|---|---|---|
| (404.4) | Found | C 50.73 | H 3.98 | N 13.68 |

28. [4-[5-(4-Methoxyphenyl)-2-pyrimidinyl]-1-pyridinium]dicyanomethide (115)

The solution of 0.53 g (2 mmol) of 87 in 50 ml of boiling, anhydrous toluene was admixed with a suspension of 0.30 g (2.08 mmol) of tetracyanoethylene oxide[121] in 50 ml of anhydrous toluene, an orange precipitate being formed, and the mixture was refluxed for 15 min. After a little water had been added, the mixture was refluxed for a further 5 min. After cooling, the precipitate was filtered off with suction, washed with water and methanol and recrystallized from 50 ml of DMF. Yield 0.46 g (70%); orange needles, m.p. 334°–335° C.

IR (KBr): ν=2188 cm$^{-1}$, 2158, 1624, 1608, 1577, 1520, 1502, 1428, 1254, 1191, 832, 792. - UV (CH$_3$CN): λ$_{max}$ (log ε)=238 nm (4.147), 250 (sh, 4.046), 290 (sh, 3.828), 330 (4.029), 454 (4.720). - UV (CHCl$_3$): λ$_{max}$ (log ε)=340 nm (3.940), 469 (4.713). -UV (CF$_3$COOH): λ$_{max}$ (log ε)=370 nm (sh, 3.916), 487 (4.576). - $^1$H NMR ([D$_6$]DMSO): δ=3.84 (s, 3H, OCH$_3$), 7.14 (d, J=8.9 Hz, 2H, CCHCH-COCH$_3$), 7.89 (d, J=8.9 Hz, 2H, CCHCHCOCH$_3$), 8.60 (d, J=7.4 Hz, 2H, N$^+$CHCH), 8.67 (d, J=7.4 Hz, 2H, N$^+$CHCH), 9.33 (s, 2H, pyrimidinyl-H). - $^1$H NMR (CF$_3$COOH): δ=4.02 (s, 3H, OCH$_3$), 7.24 (d, 2H, CCHCHCOCH$_3$), 7.80 (d, 2H, CCHCHCOCH$_3$), 8.70 (d, 2H, N$^+$CHCH), 8.85 (d, 2H, N$^+$CHCH), 9.50 (s, 2H, pyrimidinyl-H). -MS (70 eV):m/z (%) =327 (100) [M$^+$], 312 (9) [M$^+$- CH$_3$], 263 (57) [M$^+$-C(CN)$_2$]. - TLC (AcOEt): R$_f$=0.88.

| C$_{19}$H$_{13}$N$_5$O | Calc. | C 69.72 | H 4.00 | N 21.39 |
|---|---|---|---|---|
| (327.4) | Found | C 69.59 | H 4.06 | N 21.24 |

29. [4-[5-(4-Nitrophenyl)-2-pyrimidinyl]-1-pyridinium]dicyanomethide (116)

As described under 28, from 0.556 g (2 mmol) of 88 and 0.3 g (2.08 mmol) of tetracyanoethylene oxide[121]. Yield 0.56 g (82%); orange powder, m.p. >350° C.

IR (KBr): ν=2188 cm$^{-1}$, 2155, 1624, 1600, 1577, 1517, 1429, 1347, 1275, 1192, 856, 795. - UV (CH$_3$CN): λ$_{max}$ (log ε)=301 nm (4.311), 459 (4.685). - UV (CHCl$_3$): λ$_{max}$ (log ε)=302 nm (4.261), 477 (4.692). -UV (CF$_3$COOH): λ$_{max}$ (log ε)=290 nm (sh, 4.254), 308 (4.299), 460 (4.333), 480 (sh, 4.315). - $^1$H NMR ([D$_6$]DMSO): δ=8.03 (d, 2H, CCHCHCNO$_2$), 8.22 (d, 2H, CCHCHCNO$_2$), 8.50 (s, 4H, pyridinium-H), 9.25 (s, 2H, pyrimidinyl-H). - $^1$H NMR (CF$_3$COOH): δ=7.98 (d, 2H, CCHCHCNO$_2$), 8.48 (d, 2H, CCHCHCNO$_2$), 8.87 (m, 4H, pyridinium-H), 9.53 (s, 2H, pyrimidinyl-H). - MS (70 eV): m/z (%)=342 (74) [M$^+$], 312 (42) [M$^+$- NO], 296 [M$^+$- NO$_2$], 278 (50) [M$^+$- C(CN)$_2$], 248 (100) [M$^+$- ONC (CN)$_2$]. - TLC (AcOEt): R$_f$=0.90.

| C$_{18}$H$_{10}$N$_6$O$_2$ | Calc. | C 63.16 | H 2.94 | N 24.55 |
|---|---|---|---|---|
| (342.3) | Found | C 63.51 | H 3.04 | N 24.32 |

30. [4-[2-(4-Methoxyphenyl)-5-pyrimidinyl]-1-pyridinium]dicyanomethide (117)

As described under 28, from 0.53 g (2 mmol) of 90 and 0.30 g (2.08 mmol) of tetracyanoethylene oxide[121]. Recrystallization was carried out from 50 ml of DMF. Yield 0.53 g (81%); small felted orange needles, m.p. 5° C. (decomp.).

IR (KBr): ν=2185 cm$^{-1}$, 2153, 1631, 1606, 1579, 1545, 1514, 1431, 1262, 1210, 1168, 832, 799. - UV (CH$_3$CN): λ$_{max}$ (log ε)=300 nm (sh, 4.140), 322 (4.261), 443 (4.618). UV (CHCl$_3$): λ$_{max}$ (log ε)=310 nm (sh, 3.956), 343 (4.156), 461 (4.674). - UV (CF$_3$COOH): λ$_{max}$ (log ε)=370 nm (sh, 4.223), 438 (4.570). - $^1$H NMR ([D$_6$]DMSO): δ=3.81 (s, 3H, OCH$_3$), 7.03 (d, 2H, CCHCHCOCH$_3$), 8.18 (d, 2H, N$^+$CHCH), 8.33 (d, 2H, CCHCHCOCH$_3$), 8.48 (d, 2H, N$^+$CHCH), 9.25 (s, 2H, pyrimidinyl-H). - $^1$H NMR (CF$_3$COOH): δ=4.00 (s, 3H, OCH$_3$), 7.20 (d, 2H, CCHCH-COCH$_3$), 8.25–8.47 (m, 4H, CCHCHCOCH$_3$ and N$^+$CHCH), 8.87 (d, 2H, N$^+$CHCH), 9.54 (s, 2H, pyrimidinyl-H). - MS (70 eV): m/z (%)=327 (100) [M$^+$], 312 (4) [M$^+$- CH$_3$], 263 (57) [M$^+$- C(CN)$_2$]. - TLC (CH$_2$Cl$_2$/methanol 10/1): R$_f$=0.62.

| C$_{19}$H$_{13}$N$_5$O | Calc. | C 69.72 | H 4.00 | N 21.39 |
|---|---|---|---|---|
| (327.4) | Found | C 69.56 | H 4.28 | N 21.34 |

31. [4-[2-(4-Nitrophenyl)-5-pyrimidinyl]-1-pyridinium]dicyanamethide (118)

As described under 28, from 0.56 g (2 mmol) of 91 and 0.30 g (2.08 mmol) of tetracyanoethylene oxide[121]. Recrystallization was carried out from 70 ml of DMF. Yield 0.51 g (74%); red powder, m.p. >350° C.

IR (KBr): ν=2193 cm$^{-1}$, 2159, 1630, 1601, 1550, 1519, 1435, 1345, 1282, 1215, 855, 827, 744. -UV (CH$_3$CN): λ$_{max}$ (log ε)=298 nm (4.418), 345 (sh, 3.613), 450 (4.582). - UV (CHCl$_3$): $\lambda_{max}$ (log ε)=303 nm (4.399), 345 (sh, 3.480), 465 (4.618). - UV (CF$_3$COOH): $\lambda_{max}$ (log ε)=300 nm (4.422), 447 (4.338). - $^1$H NMR ([D$_6$]DMSO): δ=8.17–8.31 (m, 4H, CCHCHCNO$_2$ and N$^+$CHCH), 8.43–8.62 (m, 4H, CCHCHCNO$_2$ and N$^+$CHCH) , 9.30 (s, 2H, pyrimidinyl-H). - $^1$H NMR (CF$_3$COOH): δ=8.39 (d, 2H, CCHCHCNO$_2$), 8.56 (s, 4H, pyridinium-H), 8.91 (d, 2H, CCHCHCNO$_2$), 9.80 (s, 2H, pyrimidinyl-H). - MS (70 eV): m/z (%)=342 (18) [M$^+$], 312 (12) [M$^+$- NO], 296 (3) [M$^+$- NO$_2$], 278 (26) [M+-C(CN)$_2$], 248 (100) [M$^+$- ONC(CN)$_2$].

| C$_{18}$H$_{10}$N$_6$O$_2$ (342.3) | Calc. Found | C 63.16 C 63.48 | H 2.94 H 3.15 | N 24.55 N 24.34 |
|---|---|---|---|---|

32. 1-[2-(4-Methoxyphenyl)-5-pyrimidinyl]-pyridinium tetrafluoroborate (124)

As described under 12, from 1.52 g (4 mmol) of 123$^6$ and 1.12 g (6 mmol) of 4-methoxybenzamidine hydrochloride$^{132}$ in 12 ml of anhydrous pyridine. Recrystallization was carried out from acetonitrile/ether. Yield 0.59 g (42%); flesh-colored powder, m.p. 223°–225° C.

IR (KBr): ν=1630 cm$^{-1}$, 1608, 1581, 1476, 1433, 1252, 1084, 791. -UV (CH$_3$CN): $\lambda_{max}$ (log ε)=233 nm (4.084), 268 (4.059), 320 (4.335) . - UV (CHCl$_3$) , qual.: $\lambda_{max}$=285 nm, 340. - $^1$H NMR ([D$_6$]DMSO): δ=3.85 (s, 3H, OCH$_3$), 7.09 (d, 2H, CCHCHCOCH$_3$), 8.25–8.45 (m, 4H, N$^+$CHCHCH and CCHCHCOCH$_3$), 8.80 (t, 1H, N$^+$CHCHCH), 9.27 (s, 2H, pyrimidinyl-H), 9.37 (d, 2H, N$^+$CHCHCH).

| C$_{16}$H$_{14}$BF$_4$N$_3$O (351.1) | Calc. Found | C 54.73 C 55.33 | H 4.02 H 4.09 | N 11.97 N 11.93 |
|---|---|---|---|---|

33. 1-[2-(4-Nitrophenyl)-5-pyrimidinyl]-pyridinium tetrafluoroborate (125)

The suspension of 1.14 g (3 mmol) of 123$^6$ in 9 ml of anhydrous pyridine was admixed with 0.91 g (4.5 mmol) of 4-nitrobenzamidine hydrochloride$^{131}$, and the mixture was stirred overnight at room temperature. The reaction mixture was then poured onto ice/concentrated sulfuric acid (60 g/11.1 ml), the precipitate was filtered off with suction, washed with water and recrystallized from acetonitrile/ether. Yield 0.37 g (34%); colorless platelets, m.p. 208°–209° C.

IR (KBr): ν=1630 cm$^{-1}$, 1608, 1575, 1556, 1524, 1477, 1433, 1344, 1084, 804, 744, 682. -UV (CH$_3$CN): $\lambda_{max}$ (log ε) =290 nm (4.459). - UV (CHCl$_3$), qual.: $\lambda_{max}$=294 nm. - $^1$H NMR ([D$_6$]DMSO): δ=8.45 (dd, 2H, N$^+$CHCHCH), 8.46 (d, J=9.0 Hz, 2H, CCHCHCNO$_2$), 8.75 (d, J=9.0 Hz, 2H, CCHCHCNO$_2$), 8.91 (t, J=7.7 Hz, 1H, N$^+$CHCHCH), 9.48 (d, J=5.6 Hz, 2H, N$^+$CHCHCH), 9.53 (s, 2H, pyrimidinyl-H) . - $^{13}$C NMR ([D$_6$]DMSO): δ=124.21 (d, $^1J_{C,H}$=170.6 Hz, $^3J_{C,H}$=4.5 Hz, nitrophenyl C-3 and C-5) 128.13 (d, $^1J_{C,H}$=178.6 Hz pyridinium C-3 and C-5) 129.61 (d, $^1J_{C,H}$= 168.2 Hz, $^3J_{C,H}$=6.5 Hz), 136.62 (s nitrophenyl C-1) 141.09 (s, $^3J_{C,H}$=7.6 Hz, pyridinium C-5), 145.17 (d, $^1J_{C,H}$=195 Hz, pyridinium C-2 and C-6) 147.77 (d, $^1J_{C,H}$= 172.8 Hz, $^3J_{C,H}$=5.9 Hz, pyridinium C-4), 149.53 (s, $^3J_{C,H}$ =9.7 Hz, $^3J_{C,H}$=3.3 Hz, nitrophenyl C-4), 154.27 (d, $^1J_{C,H}$=192.1 Hz, $^3J_{C,H}$=3.2 Hz, pyrimidinyl C-4 and C-6), 162.61 (s, $^3J_{C,H}$= 10.4 Hz and 3.9 Hz pyrimidinyl C-2).

| C$_{15}$H$_{11}$BF$_4$N$_4$O$_2$ (366.1) | Calc. Found | C 49.21 C 49.29 | H 3.03 N 3.12 | N 15.30 N 15.08 |
|---|---|---|---|---|

34. 1-[2-(4-Pyridyl)-5-pyrimidinyl]-pyridinium tetrafluoroborate (126)

The suspension of 3.03 g (8 mmol) of 123$^6$ in 25 ml of anhydrous pyridine was admixed with 1.58 g (12 mmol) of 4-pyridinecarbamidine hydrochloride$^{110}$ and the mixture was heated to 80° C. for 5 h. The precipitate formed upon cooling was filtered off with suction, washed with water and recrystallized from acetonitrile/isopropanol. Yield 1.27 g (49%); colorless crystal flakes, m.p. 280°–282° C. (decomp.).

IR (KBr): ν=3044 cm$^{-1}$, 1640, 1629, 1600, 1547, 1474, 1435, 1084, 784. - UV (CH$_3$CN): $\lambda_{max}$ (log ε)=262 nm (4.408), 310 (sh, 3.426) . - UV (CHCl$_3$), qual.: $\lambda_{max}$=265 nm (broad). - $^1$H NMR ([D$_6$]DMSO): δ=8.30–8.50 (m, 4H, pyridinyl-NCHCH and pyridinium-N$^+$CHCHCH), 8.80–8.97 (m, 3H, pyridinyl-NCHCH and pyridinium-N$^+$CHCHCH), 9.45 (d, 2H, pyridinium-N$^+$CHCHCH), 9.500 (s, 2H, pyrimidinyl-H).

| C$_{14}$H$_{11}$BF$_4$N$_4$ (322.1) | Calc. Found | C 52.21 C 52.09 | H 3.44 H 3.49 | N 17.40 N 17.48 |
|---|---|---|---|---|

35. 1-[2-(1-Dicyanomethido-4-pyridinio)-5-pyrimidinyl]pyridinium tetrafluoroborate (127)

The solution of 0.48 g (1.5 mmol) of 126 in 15 ml of boiling anhydrous acetonitrile was admixed with a solution of 0.23 g (1.6 mmol) of tetracyanoethylene oxide$^{121}$ in 10 ml of anhydrous acetonitrile, and the mixture was refluxed for 15 min. After the addition of a little water, the mixture was refluxed for a further 5 min. The black-red solution formed was stored, after cooling, overnight at −20° C., which produced a precipitate which was filtered off with suction and recrystallized from 40 ml of acetonitrile. Yield 0.36 g (62%); brown crystal powder, m.p. 265° C. (decomp.).

IR (KBr): ν=3122 cm$^{-1}$, 3071, 2186, 2155, 1628, 1576, 1478, 1431, 1279, 1196, 1084, 795. - UV (CH$_3$CN): $\lambda_{max}$ (log ε)=255 nm (4.335), 280 (sh, 3.944), 348 (3.407), 468 (4.601). -UV (CF$_3$COOH): $\lambda_{max}$ (log ε)=263 nm (4.430), 325 (sh, 3.096), 448 (4.247). - $^1$H NMR ([D$_6$]DMSO): δ= 8.36 (m, 2H, N$^+$CHCHCH), 8.60 (s, 4H, N$^+$CHCHC), 8.86 (t, 1H, N$^+$CHCHCH), 9.40 (d, 2H, N+CHCHCH), 9.45 (s, 2H, pyrimidinyl-H).

| C$_{17}$H$_{11}$BF$_4$N$_6$ (386.1) | Calc. Found | C 52.88 C 52.51 | H 2.87 H 2.80 | N 21.77 N 21.56 |
|---|---|---|---|---|

36. N-(4-Methoxybenzylidene)-4-[2-(4-pyridyl)-5-pyridinyl]-aniline (128)

The suspension of 0.25 g (1 mmol) of 97 in 80 ml of anhydrous toluene was admixed with 1 ml (8.24 mmol) of 4-methoxybenzaldehyde and a trace of p-toluenesulfonic acid, and the mixture was refluxed for 24 h in a water separator. The precipitate formed after cooling was filtered off with suction, washed with toluene and recrystallized from 100 ml of toluene. Yield 0.30 g (82%); pale yellow powder, m.p. 214°–216° C.

IR (KBr): ν=3033 cm⁻¹, 1620, 1608, 1590, 1570, 1514, 1437, 1261, 1166, 846, 784. - UV (CH₃CN), qual.: λ_max= 260 mm (sh), 310 (sh), 339. - UV (DMSO): λ_max (log ε)= 300 nm (sh, 4.304), 347 (4.726) . - UV (CF₃COOH): λ_max (log ε)=275 nm (broad, 4.094), 388 (4.737). - ¹H NMR (CF₃COOH): δ=4.09 (s, 3H, OCH₃), 7.31 (d, J=8.6 Hz, 2H, CCHCHCOCH₃), 7.93 (d, J=9.3 Hz, 2H, CCHCHCN), 8.09 (d, J=9.3 Hz, 2H, CCHCHCN), 8.27 (d, J=8.6 Hz, 2H, CCHCHCOCH₃), 8.90–9.20 (m, 5H, pyridyl-H and methine-H), 9.57 (s, 2H, pyrimidinyl-H). -MS (70 eV) m/z (%)=366 (100) [M⁺]. - TLC (CH₃Cl₂/methanol 10/1): R_f=0.53.

| C₂₃H₁₈N₄O | Calc. | C 75.39 | H 4.95 | N 15.29 |
|---|---|---|---|---|
| (366.4) | Found | C 75.82 | H 4.96 | N 15.12 |

37. 4-Methoxybenzaldehyde-4-[2-(4-pyridyl)-5-pyrimidinyl]-phenylhydrazone (129)

As described under 36, from 0.26 g (1 mmol) of 100, 1 ml (8.24 mmol) of 4-methoxybenzaldehyde and a trace of p-toluenesulfonic acid in 80 ml of anhydrous toluene. Recrystallization was dispensed with, as decomposition was observed in a test in toluene. Yield 0.27 g (71%); orange-brown powder, m.p. 194°–196° C.

IR (KBr): ν=3315 cm⁻¹, 3280, 1608, 1572, 1528, 1512, 1432, 1297, 1251, 828, 785. -UV (CH₃CN): λ_max (log ε)= 247 nm (4.390), 296 (4.102), 377 (4.588). -UV (DMSO): λ_max (log ε)=300 nm (4.091), 397 (4.552). - UV (CF₃COOH): λ_max (log ε)=353 nm (broad, 4.449), 400 (sh, 4.305). -¹H NMR ([D₆]DMSO): δ=3.77 (s, 3H, OCH₃), 6.96 (d, J= 8.7 Hz, 2H, CCHCHCNH) , 7.19 (d, J=8.5 Hz, 2H, CCHCHCOCH₃), 7.61 (d, J=8.7 Hz, 2H, CCHCHCNH), 7.77 (d, J=8.5 Hz, 2H, CCHCHCOCH₃) , 7.89 (s, 1H, methine-H) , 8.27 (d, J=5.2 Hz, 2H, NCHCH), 8.76 (d, J=5.2 Hz, 2H, NCHCH), 9.24 (s, 2H, pyrimidinyl-H), 10.44 (s, 1H, NH). - 381 (100) [M⁺], 247 (48) [M⁺ - NCHC₆H₄OCH₃]. - TLC (CH₂Cl₂/methanol 10/1): R_f=0.46.

| C₂₃H₁₉N₅O | Calc. | C 72.42 | H 5.02 | N 18.36 |
|---|---|---|---|---|
| (381.4) | Found | C 72.08 | H 5.02 | N 18.23 |

38. 2-(4-Nitrophenyl)-5-(4-octadecyloxyphenyl)-pyrimidine (131)

As described under 39, from 0.59 g (2 mmol) of 82, 0.73 g (2.2 mmol) of octadecyl bromide and 0.21 g (2.2 mmol) of potassium carbonate in 150 ml of ethanol. The crude product was purified by column chromatography (silica gel, methylene chloride), followed by recrystallization from petroleum ether. Yield 0.45 g (41%); flocculent, pale yellow powder, m.p. 116° C., clearing point 225°–226° C.

IR (KBr): ν=2917 cm⁻¹, 2851, 1610, 1539, 1519, 1473, 1434, 1343, 1254, 1185, 828, 743. -UV (CH₃CN), qual.: λ_max =257 nm, 333. - UV (CHCl₃): λ_max (log ε)=259 nm (4.221), 335 (4.365) . - ¹H NMR (CDCl₃): δ=1.15–1.45 (m, 35H, OCH₂C₁₇H₃₅) , 3.99 (t, 2H, OCH₂C₁₇H₃₅), 7.00 (d, 2H, CCHCHCOC₁₈H₃₇), 7.52 (d, 2H, CCHCHCOC₁₈H₃₇) , 8.27 (d, 2H, CCHCHCNO₂), 8.61 (d, 2H, CCHCHCNO₂), 8.95 (s, 2H, pyrimidine-H). -MS (70 eV):m/z (%)=545 (74) [M⁺], 515 (17) [M⁺ - NO], 293 (100) [M⁺ - C₁₈H₃₆]. - TLC (CH₂Cl₂): R_f=0.58.

| C₃₄H₄₇N₃O₃ | Calc. | C 74.83 | H 8.68 | N 7.70 |
|---|---|---|---|---|
| (545.8) | Found | C 74.99 | H 8.81 | N 7.77 |

39. 5-(4-Octadecyloxyphenyl)-2-(4-pyridyl)-pyrimidine (132)

1.50 g (6 mmol) of 89 (finely powdered) were heated to boiling with 0.61 g (6.2 mmol) of potassium carbonate in 400 ml of ethanol, until a clear yellow solution had formed, which was then admixed with 2.17 g (6.5 mmol) of molten octadecyl bromide. The mixture was refluxed for a further 20 h, allowed to cool, and the reaction mixture was stored overnight at −20° C. The precipitate formed was filtered off with suction and recrystallized from ligroin. Yield 1.00 g (33%); waxy, colorless powder, m.p. 117°–118° C., clearing point 127° C.

IR (KBr): ν=3037 cm⁻¹, 2918, 2850, 1608, 1596, 1519, 1441, 1290, 1264, 1257, 833, 787. -UV (CH₃CN), qual.: λ_max=301 mn, 370 (sh). - UV (CHCl₃): λ_max (log ε)=303 nm (4.325), 330 (sh, 4.201), 370 (sh, 3.234). - ¹H NMR (CDCl₃): δ=1.15–1.45 (m, 35H, OCH₂C₁₇H₃₅) , 3.97 (t, 2H, OCH₂C₁₇H₃₅), 7.01 (d, 2H, CCHCHCOC₁₈H₃₇), 7.54 (d, 2H, CCHCHCOC₁₈H₃₇), 8.47 (d, 2H, NCHCH), 8.74 (d, 2H, NCHCH), 9.00 (s, 2H, pyrimidine-H). -MS (70 eV): m/z (%)=501 (61) [M⁺], 249 (100) . - TLC (CH₂Cl₂/methanol 1/1): R_f= 0.65.

| C₃₃H₄₇N₃O | Calc. | C 79.00 | H 9.44 | N 8.37 |
|---|---|---|---|---|
| (501.8) | Found | C 78.79 | H 9.37 | N 8.42 |

40. 4-[5-(4-Methoxyphenyl)-2-pyrimidinyl]-1-octadecylpyridinium bromide (133)

The solution of 1.32 g (5 mmol) of 87 in 50 ml of boiling toluene was admixed with 1.83 g (5.5 mmol) of molten octadecyl bromide, and the mixture was refluxed for 4 days. The yellow solution formed was cooled and then stored overnight at −20° C., the precipitate formed was filtered off with suction and washed with diethyl ether. Unreacted starting compound was leached from the crude product by column chromatography on silica gel with toluene/ethyl acetate 1/1 (R_f=0.31) and the product was then eluted from the column with methylene chloride/methanol 10/1. After the solvents had been distilled off, recrystallization was carried out from toluene. Yield 1.05 g (35%); flocculent, yellow powder, m.p. 158°–160° C., clearing point 194°–196° C.

IR (KBr): ν=3033 cm⁻¹, 2917, 2850, 1640, 1610, 1576, 1534, 1519, 1471, 1431, 1384, 1262, 833, -UV (CH₃CN): λ_max (log ε)=245 nm (4.274), 355 (4.296). - UV (CHCl₃): λ_max (log ε)=250 nm (4.280), 370 (4.274). - ¹H NMR (CDCl₃): δ=1.10–1.40 (m, 35H, N⁺CH₂C₁₇H₃₅) , 3.86 (s, 3H, OCH₃) , 5.12 (t, J=6.2 Hz, 2H, N⁺CH₂C₁₇H₃₅), 7.05 (d, J=8.8 Hz, 2H, CCHCHCOCH₃), 7.58 (d, J=8.8 Hz, 2H, CCHCHCOCH₃), 8.96 (d, J=6.1 Hz, 2H, N⁺CHCH), 9.06 (s, 2H, pyrimidinyl-H), 9.62 (d, J=6.1 Hz, 2H, N⁺CHCH). -

TLC (CH$_2$Cl$_2$/methanol 10/1): R$_f$=0.50.

| C$_{34}$H$_{50}$BrN$_3$O | Calc. | C 68.44 | H 8.45 | N 7.04 |
|---|---|---|---|---|
| (596.7) | Found | C 67.84 | H 8.47 | N 7.01 |

41. 1-Methyl-4-[5-(4-octadecyloxyphenyl)-2-pyrimidinylene]-pyridinium methyl sulfate (134)

0.40 g (0.797 mmol) of 132 was heated in 50 ml of toluene until a clear solution had formed, which was then admixed with 0.08 ml (0.852 mmol) of dimethyl sulfate, the solution turning yellow in the process. The mixture was refluxed for a further 2 h, allowed to cool and the react ion mixture was stored overnight at −20° C. The precipitate formed was filtered off with suction, washed with toluene and recrystallized from 50 ml of ethanol. Yield 0.45 g (90%); flocculent, pale yellow powder, m.p. 126°–127° C., clearing point 239°–241° C.

IR (KBr): ν=2920 cm$^{-1}$, 2851, 1640, 1610, 1536, 1520, 1469, 1434, 1257, 1009, 834, 792, 769. - UV (CH$_3$CN), qual.: λ$_{max}$=244 nm, 357. -UV (CHCl$_3$): λ$_{max}$ (log ε)=253 nm (4.265), 376 (4.264). - $^1$H NMR (CDCl$_3$): δ=1.15–1.45 (m, 35H, OCH$_2$C$_{17}$H$_{35}$), 3.69 (s, 3H, methyl sulfate), 3.97 (t, 2H, OCH$_2$C$_{17}$H$_{35}$), 4.62 (s, 3H, N$^+$CH$_3$), 6.95 (d, 2H, CCHCHCOC$_{18}$H$_{37}$), 7.50 (d, 2H, CCHCHCOC$_{18}$H$_{37}$), 8.80 (d, 2H, N$^+$CHCH), 9.16 (d, 2H, N$^+$CHCH). - TLC (CH$_2$Cl$_2$/methanol 10/1): R$_f$=0.11.

| C$_{35}$H$_{53}$N$_3$O$_5$S | Calc. | C 66.95 | H 8.51 | N 6.69 |
|---|---|---|---|---|
| (627.9) | Found | C 66.31 | H 8.30 | N 6.56 |

42. N-(4-Octadecyloxybenzylidene)-4-[2-(4-pyridyl)-5-pyrimidinyl]-aniline (135)

As described under 36, from 0.50 g (2 mmol) of 97, 1.00 g (2.67 mmol) of p-octadecyloxybenzaldehyde, and a trace of p-toluenesulfonic acid in 160 ml of anhydrous toluene. Recrystallization was carried out from 200 ml of petroleum ether. Yield 0.92 g (76%); ivory-colored powder m.p 117°–119° C., clearing point 255°–257° C.

IR (KBr): ν=3037 cm$^{-1}$, 2918, 2850, 1622, 1609, 1594, 1574, 1523, 1514, 1439, 1257, 1170, 846, 784. - UV (CH$_3$CN), qual.: λ$_{max}$=277 (CHCl$_3$): λ$_{max}$ (log ε)=260 nm (4.114), 310 (sh, 4.435), 342 (4.584).

Formulae of starting materials

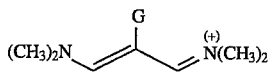

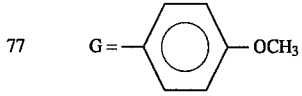
77   G =

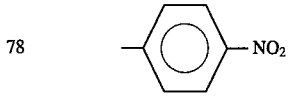
78

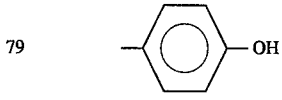
79

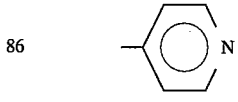
86

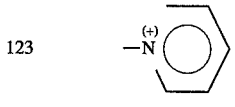
123

Literature references for starting materials

6. D. Lloyd, K. S. Tucker, J. Chem. Soc., Perkin Trans. I 1981, 726.
110. B. Singh, G. Y. Lesher, J. Heterocycl. Chem. 1977, 14, 1413.
111. a) Z. Arnold, Collect. Czech. Chem. Commun. 1963, 28, 863.
b) H. Niedrich, H. -U. Heyne, E. Schrötter, H. -J. J änsch, H. J. Heidrich, G. Faust, D. Lohmann, Pharmazie 1986, 41, 173.
121. W. J. Linn, O. W. Webster, R. E. Benson, J. Am. Chem. Soc,, 1965, 87, 3651.
123. C. Bubeck, A. Laschewsky, D. Lupo, D. Neher, P. Ottenbreit, W. Paulus, W. Prass, H. Ringsdorf, G. Wegner, Adv. Mater. 1991, 3, 54
130. S. N. Balasubrahmanyam, A. S. Radhakrishna, J. Chem. Soc., Perkin Trans. 2 1977, 1388
131. V. B. Piskov, V. P. Kasperovich, Zh. Org. Khim. 1978, 14, 830, J. Org. Chem. USSR (Engl. Transl.) 1978, 14, 758.
132. H. Pischel, A. Holy, G. Wagner, Collect. Czech. Chem. Commun. 1981, 46, 933.
133. D. Lloyd, C. Reichardt, M. Struthers, Justus Liebigs Ann. Chem. 1986, 1368.

We claim:
1. A non-linear optical material comprising a compound having a pyrimidine ring, of the formula (I)

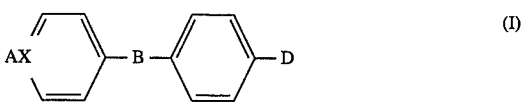
(I)

in which AX is selected from the group consisting of

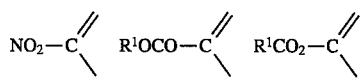

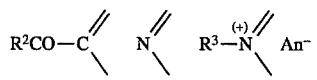

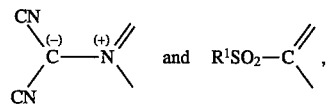

and

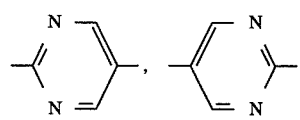

An⁻ is an anion,
B is

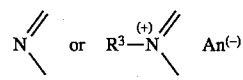

D is selected from the group consisting of
— NH$_2$
— NH—NH$_2$
— OR$^6$
— O(CH$_2$)$_p$OH
— OH
— NR$^5$R$^6$
— NHR$^6$
— N=CH—R$^4$
— HN—N=CH—R$^4$ and
— NO$_2$, the radicals R$^1$, R$^2$, R$^3$ and R$^5$ are an alkyl radical having from 1 to 22 carbon atoms or a radical CF$_3$(CF$_2$)$_m$(CH$_2$)$_n$, where m is an integer of at least 5, n is an integer of at least zero, and (n+m) is at most 22, R$^4$ is a alkylphenyl or alkoxyphenyl radical whose alkyl groups contain from 4 to 22 carbon atoms, R$^6$ is an alkyl radical having from 1 to 22 carbon atoms or the radical CF$_3$(CF$_2$)$_m$(CH$_2$)$_n$, where m is an integer of at least 5, n is an integer of at least zero, and (n+m) is at most 22, or the group (CH$_2$)$_p$OH, where p is an integer from 2 to 5 except compounds containing two nitro groups.

2. A compound of the formula

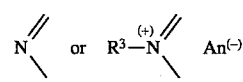

wherein D is NO$_2$ and,
AX is

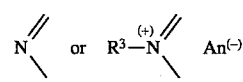

R$^3$ is an alkyl radical having from 1 to 22 carbon atoms or a radical CF$_3$(CF$_2$)$_m$(CH$_2$)$_n$, where m is an integer of at least 5 and n is an integer of at least zero and (n+m) is at most 22, and An$^{(-)}$ is an anion, and B is

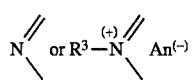

3. A compound having the formula II

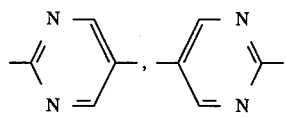 (II)

wherein
AX is

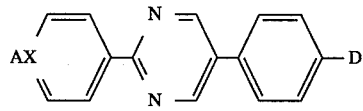

An$^{(-)}$ is an anion,
D is OR$^2$, OH, NH$_2$, NH—NH$_2$,
R$^4$—CH=N— or
R$^4$—CH=N—NH—

R$^2$, R$^3$ is an alkyl radical having from 1 to 22 carbon atoms or a radical CF$_3$(CF$_2$)$_m$(CH$_2$)$_n$, where m is an integer of at least 5 and n is an integer of at least zero and (n+m) is at most 22, R$^4$ is a alkylphenyl or alkoxyphenyl radical whose alkyl groups contain from 4 to 22 carbon atoms.

4. A compound having the formula III

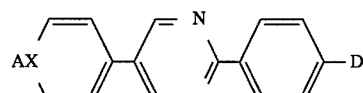 (III)

wherein
AX is

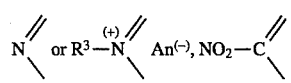

R$^3$ is an alkyl radical having from 1 to 22 carbon atoms or a radical CF$_3$(CF$_2$)$_m$(CH$_2$)$_n$, where m is an integer of at least 5 and n is an integer of at least zero and (n+m) is at most 22, D is —OR$^6$ or —N=CH—R$^4$ and R$^4$ is a phenyl radical which may be substituted R$^6$ is an alkyl radical having from 1 to 22 carbon atoms or the radical CF$_3$(CF$_2$)$_m$(CH$_2$)$_n$, where m is an integer of at least 5, n is an integer of at least zero, and (n+m) is at most 22, or the group (CH$_2$)$_p$OH, where p is an integer from 2 to 5.

5. A compound of the formula IV

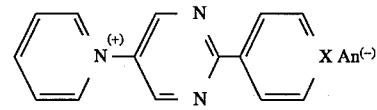 (IV)

wherein

X is

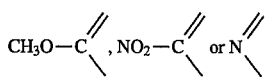

and An$^{(-)}$ is an anion.

6. A compound of formula I

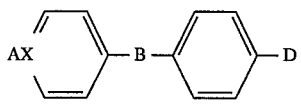  (I)

in which

AX is

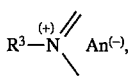

An$^-$ is an anion,

B is

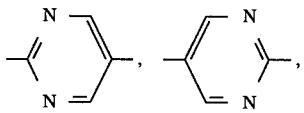

D is selected from the group consisting of
—NH$_2$
—NH—NH$_2$
—OR$^6$
—O(CH$_2$)$_p$OH
—OH
—NR$^5$R$^6$
—NHR$^6$
—N=CH—R$^4$
—HN—N=CH—R$^4$ and
—NO$_2$, R$^4$ is a alkylphenyl or alkoxyphenyl radical whose alkyl group contains from 4 to 22 carbon atoms R$^5$ is an alkyl radical having from 1 to 22 carbon atoms or the radical CF$_3$(CF$_2$)$_m$(CH$_2$)$_n$, where m is an integer of at least 5, n is an integer of at least zero, and (n+m) is at most 22, R$^6$ is an alkyl radical having from 1 to 22 carbon atoms or the radical CF$_3$(CF$_2$)$_m$(CH$_2$)$_n$, where m is an integer of at least 5, n is an integer of at least zero, and (n+m) is at most 22, or the group (CH$_2$)$_p$OH, where p is an integer from 2 to 5 and R$^3$ is an alkyl radical having from 7 to 22 carbon atoms or the radical CF$_3$(CF$_2$)$_m$(CH$_2$)$_n$, wherein m is at least 5, n is at least zero and (n+m) is at most 22.

7. A compound of formula I

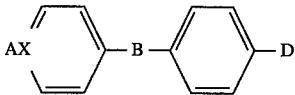  (I)

wherein

AX is selected from the group consisting of

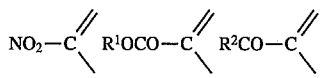

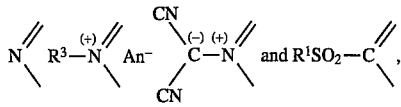

An$^-$ is an anion,

B is

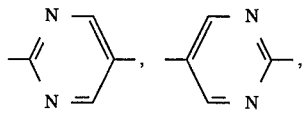

D is OR$^2$, —N=CHR$^4$, NR$^5$R$^6$, or —NH—N=CHR$^4$

R$^2$ and R$^5$ are an alkyl radical having from 4 to 22

R$^2$ and R$^5$ are an alkyl radical having from 4 to 22 carbon atoms or the radical CF$_3$(CF$_2$)$_m$—(CH$_2$)$_n$, wherein m is at least 3, n is at least zero and (n+m) is at most 22, R$^4$ is an alkylphenyl or alkoxyphenyl radical whose alkyl group contains from 4 to 22 carbon atoms and R$^6$ is hydrogen or an alkyl radical having from 1 to 22 carbon atoms.

8. A layer element containing at least one monomolecular regularly arranged layer of an amphiphilic compound on a substrate, wherein the amphiphilic compound is a compound having a pyrimidine ring, of the formula (I)

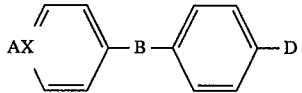  (I)

in which

AX is selected from the group consisting of

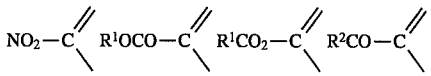

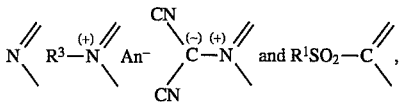

An$^-$ is an anion,

B is

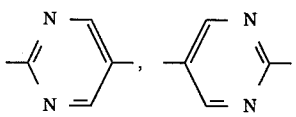

D is selected from the group consisting of
—NH$_2$
—NH—NH$_2$
—OR$^6$
—O(CH$_2$)$_p$OH
—OH
—NR$^5$R$^6$
—NHR$^6$ —N=CH—R⁴ and
—HN—N=CH⁻R⁴
—NO₂ the radicals R¹, R², R³ and R⁵ are an alkyl radical having from 1 to 22 carbon atoms or a radical CF₃(CF₂)ₘ(CH₂)ₙ, where m is an integer of at least 5, n is an integer of at least zero, and (n+m) is at most 22, R⁴ is a phenyl radical which may be substituted, R⁶ is an alkyl radical having from 1 to 22 carbon atoms or the radical CF₃(CF₂)ₘ(CH₂)ₙ, where m is an integer of at least 5, n is an integer of at least zero, and (n+m) is at most 22, or the group —(CH₂)ₚOH and p is an integer from 2 to 5.

9. A component for frequency-doubling of light, in which there is arranged on a substrate a layer of an NLO-active material, whose refractive index is higher than that of the substrate, and the component contains means for irradiation with light and reradiation of light, wherein the NLO-active material employed is a compound having a pyrimidine ring, of the formula (I)

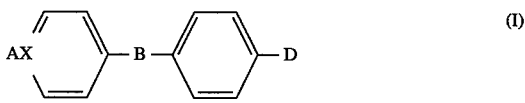
(I)

in which
AX is selected from the group consisting of

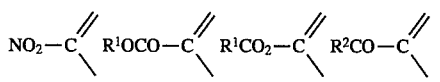

An⁻ is an anion, B is

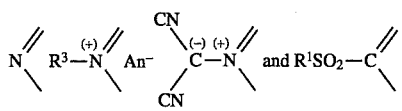

D is selected from the group consisting of
—NH₂
—NH—NH₂
—OR⁶
—O(CH₂)ₚOH
—OH
—NR⁵R⁶
—NHR⁶
—N=CH—R⁴
—HN—N=CH⁻R⁴
—NO₂ the radicals R¹, R², R³ and R⁵ are an alkyl radical having from 1 to 22 carbon atoms or a radical CF₃(CF₂)ₘ(CH₂)ₙ, where m is an integer of at least 5, n is an integer of at least zero, and (n+m) is at most 22, R⁴ is a phenyl radical which may be substituted, R⁶ is an alkyl radical having from 1 to 22 carbon atoms or the radical CF₃(CF₂)ₘ(CH₂)ₙ, where m is an integer of at least 5, n is an integer of at least zero, and (n+m) is at most 22, or the group —(CH₂)ₚOH and p is an integer from 2 to 5.

10. The component as claimed in claim 9, wherein the layer of the NLO-active material contains at least one monomolecular regularly arranged layer.

11. A non-linear optic device comprising a compound of the formula I

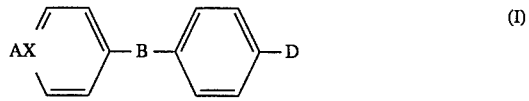
(I)

in which
AX is selected from the group consisting of

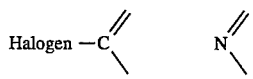

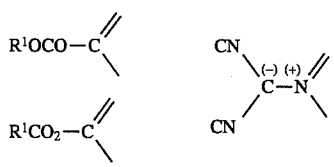

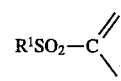

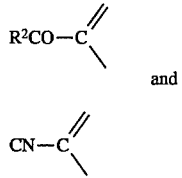

and

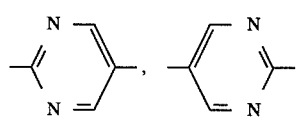

An⁽⁻⁾ is an anion
B is

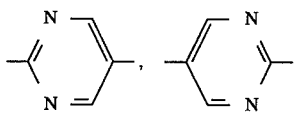

D is selected from the group consisting of
—NH₂
—NH—NH₂
—OR⁶
—O(CH₂)ₚOH
—OH
—NR⁵R⁶
—NHR⁶
—N=CH—R⁴
—HN—N=CH—R⁴
—NO₂ and
—CN, the radicals R¹, R², R³, R⁵ and R⁶ are an alkyl radical having from 1 to 22 carbon atoms or a radical CF₃(CF₂)ₘ(CH₂)ₙ, where m is at least 5, n is at least zero, and (n+m) is at most 22, the radicals R³ and R⁶ can alternatively be the group —(CH$_2$)$_p$OH and p is an integer from 2 to 5, and R$^4$ is a phenyl radical which may be substituted.

12. A process for preparing compounds of the formula V

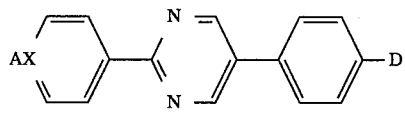
(V)

wherein

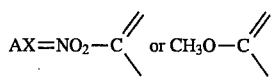

and

D=OCH$_3$, NO$_2$ or OH, which comprises reacting a vinamidinium salt of the formula VI

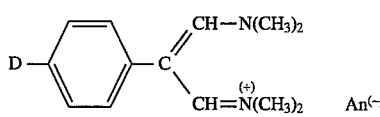
(VI)

wherein D is OCH$_3$, NO$_2$ or OH, and An$^{(-)}$ is an anion, with a benzamidine hydrochloride of the formula VII

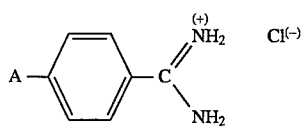
(VII)

wherein A is NO$_2$ or OCH$_3$, in anhydrous pyridine; except reacting a salt of the formula VI, wherein D is NO$_2$ with a benzamidinahydrochloride of the formula VII, wherein A is NO$_2$.

13. A process for preparing compounds of the formula VIII

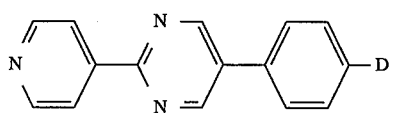
VIII wherein D=OCH$_3$, NO$_2$, or OH, which comprises reacting a vinamidinium salt of the formula IX

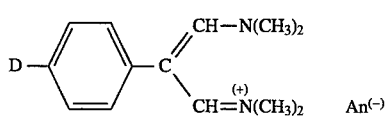
IX and An$^{(-)}$ is an anion, wherein D is OCH$_3$, NO$_2$ or OH, with 4-pyridinecarbamidine hydrochloride (formula X)

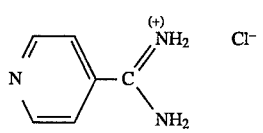
X in methanolic sodium methylate solution.

14. A process for preparing compounds of the formula (XI)

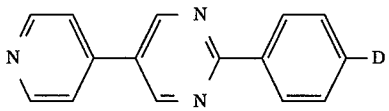
XI wherein

D=OCH$_3$ or NO$_2$, which comprises reacting a vinamidinium salt of the formula XII wherein An$^{(-)}$ is an anion

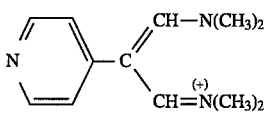
XII with a benzamidine hydrochloride of the formula XIII

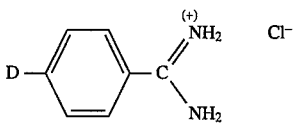
XIII wherein D is NO$_2$ or OCH$_3$, in methanolic sodium methylate solution.

15. A component in a liquid-crystal mixture, said component comprising a compound of the formula XIV

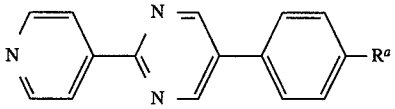
(XIV)

wherein

R$^a$ is

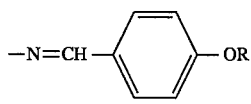

or OR and

R is a C$_4$–C$_{22}$-alkyl radical.

16. A component in a liquid-crystal mixture, said component comprising a compound of the formula XV

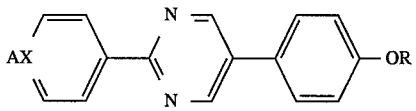
(XV)

wherein

AX is

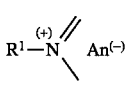

and R is methyl or

AX is

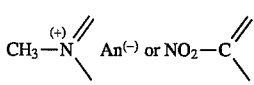

and R is R$^1$,

An$^{(-)}$ is an anion, and,

R$^1$ is a C$_4$ to C$_{22}$-alkyl radical.

17. The component as claimed in claim 15 wherein the liquid-crystal mixture is a ferroelectric liquid-crystal mixture.

18. A liquid-crystal mixture containing a compound of the formula XIV

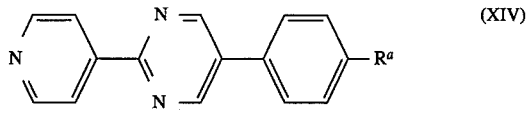

(XIV)

wherein $R^a$ is

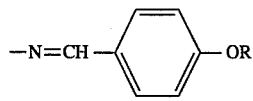

or OR and

R is a $C_{16}$–$C_{22}$-alkyl radical.

19. A liquid-crystal mixture containing a compound of the formula XV

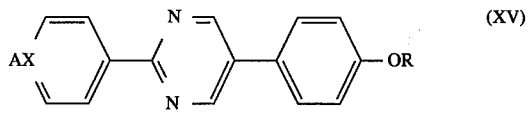

(XV)

wherein

AX is

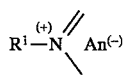

and R is methyl or

AX is

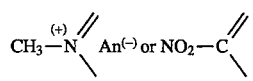

and R is $R^1$, $An^{(-)}$ is an anion, and, $R^1$ is a $C_{16}$–$C_{22}$-alkyl radical.

20. The component as claimed in claim 16 wherein the liquid-crystal mixture is a ferroelectric liquid-crystal mixture.

21. A compound having a pyrimidine ring, of the formula (I)

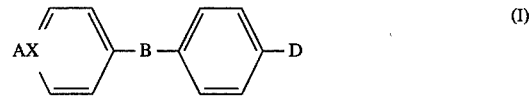

(I)

in which AX is selected from the group consisting of

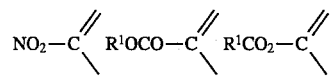

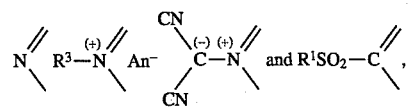

$An^-$ is an anion,

B is

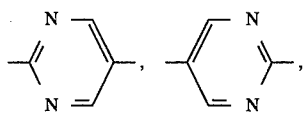

D is selected from the group consisting of

—$NH_2$

—NH—$NH_2$

—$OR^6$

—$O(CH_2)_pOH$

—OH

—$NR^5R^6$

—$NHR^6$

—N=CH—$R^4$ and

—HN—N=CH—$R^4$ the radicals $R^1$, $R^2$, $R^3$ and $R^5$ are an alkyl radical having from 1 to 22 carbon atoms or a radical $CF_3(CF_2)_m(CH_2)_n$, where m is an integer of at least 5, n is an integer of at least zero, and (n+m) is at most 22, $R^4$ is a alkylphenyl or alkoxyphenyl radical whose alkyl groups contains from 4 to 22 carbon atoms, $R^6$ is an alkyl radical having from 1 to 22 carbon atoms or the radical $CF_3(CF_2)_m(CH_2)_n$, where m is an integer of at least 5, n is an integer of at least zero, and (n+m) is at most 22, or the group —$(CH_2)_pOH$ and p is an integer from 2 to 5.

22. A compound having a pyrimidine ring, of the formula (I)

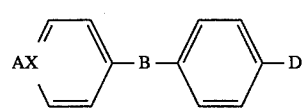

(I)

in which

AX is selected from the group consisting of

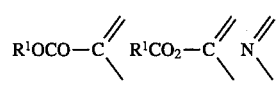

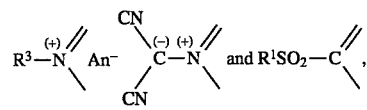

$An^-$ is an anion,

B is

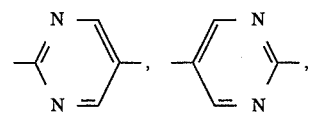

D is selected from the group consisting of

—$NH_2$

—NH —$NH_2$

—$OR^6$

—$O(CH_2)_pOH$

—OH

—$NR^5R^6$

—$NHR^6$

—N=CH—$R^4$

—HN—N=CH—$R^4$ and

—NO$_2$, the radicals $R^1$, $R^2$, $R^3$ and $R^5$ are an alkyl radical having from 1 to 22 carbon atoms or a radical $CF_3(CF_2)_m(CH_2)_n$, where m is an integer of at least 5, n is an integer of at least zero, and (n+m) is at most 22, $R^4$ is a alkylphenyl or alkoxyphenyl radical whose alkyl group contains from 4 to 22 carbon atoms, $R^6$ is an alkyl radical having from 1 to 22 carbon atoms or the radical $CF_3(CF_2)_m(CH_2)_n$, where m is an integer of at least 5, n is an integer of at least zero, and (n+m) is at most 22, or the group —$(CH_2)_p$OH and p is an integer from 2 to 5.

23. A process for preparing compounds of the formula V

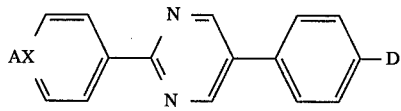

wherein

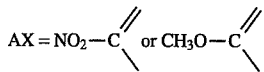

and

D=OCH$_3$ or OH, which comprises reacting a vinamidinium salt of the formula VI

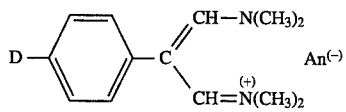

wherein D is OCH$_3$ or OH, and An$^{(-)}$ is an anion, with a benzamidine hydrochloride of the formula VII

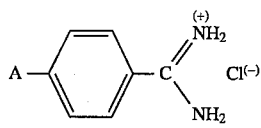

wherein A is NO$_2$ or OCH$_3$, in anhydrous pyridine.

24. A process for preparing compounds of the formula V

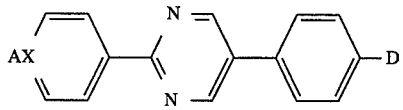

wherein

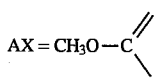

and

D=OCH$_3$, NO$_2$ or OH, which comprises reacting a vinamidinium salt of the formula VI

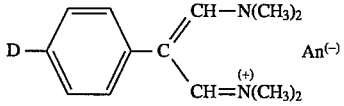

wherein D is OCH$_3$, NO$_2$ or OH, and An$^{(-)}$ is an anion, with a benzamidine hydrochloride of the formula VII

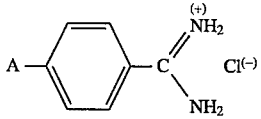

wherein A is OCH$_3$, in anhydrous pyridine.

25. The compound of claim 7 wherein $R^2$ and $R^5$ are an alkyl radical having from 7 to 22 carbon atoms.

26. The non-linear optic device of claim 11 wherein p is an integer from 2 to 3.

* * * * *